US010858357B2

(12) United States Patent
Lenkei et al.

(10) Patent No.: US 10,858,357 B2
(45) Date of Patent: Dec. 8, 2020

(54) WATER-SOLUBLE MYOSIN 2 INHIBITORS FOR THE TREATMENT OF NEUROLOGICAL, NEUROPATHIC OR PSYCHIATRIC DISEASES

(71) Applicants: PARIS SCIENCES ET LETTRES-QUARTIER LATIN, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); PRINTNET LTD., Budapest (HU)

(72) Inventors: Zsolt Lenkei, Les Molières (FR); András Málnási Csizmadia, Budapest (HU); Miklós Képiró, Siklos (HU); Boglárka Várkuti, Balatonalmadi (HU)

(73) Assignees: PARIS SCIENCES ET LETTRES-QUARTIER LATIN, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); PRINTNET LTD., Budapest (HU)

( * ) Notice: Subject to any disclaimer, the term of this patent is extended or adjusted under 35 U.S.C. 154(b) by 0 days.

(21) Appl. No.: 16/073,597

(22) PCT Filed: Jan. 27, 2017

(86) PCT No.: PCT/EP2017/051829
§ 371 (c)(1),
(2) Date: Jul. 27, 2018

(87) PCT Pub. No.: WO2017/129782
PCT Pub. Date: Aug. 3, 2017

(65) Prior Publication Data

US 2019/0084979 A1 Mar. 21, 2019

(30) Foreign Application Priority Data

Jan. 29, 2016 (EP) .................................... 16153446

(51) Int. Cl.
*C07D 471/04* (2006.01)
*A61P 25/28* (2006.01)
*A61P 25/18* (2006.01)
*A61P 25/16* (2006.01)

(52) U.S. Cl.
CPC ............ *C07D 471/04* (2013.01); *A61P 25/16* (2018.01); *A61P 25/18* (2018.01); *A61P 25/28* (2018.01)

(58) Field of Classification Search
CPC .................................................... C07D 471/04
See application file for complete search history.

(56) References Cited

U.S. PATENT DOCUMENTS

2012/0178166 A1* 7/2012 Chen ................... C12N 5/0606 435/455

OTHER PUBLICATIONS

Kepiro et al: "para-Nitroblebbistatin, the non-cytotoxic and photostable myosin II inhibitor", Angewandte Chemie, vol. 53, Jun. 20, 2014, pp. 8350-8354.

* cited by examiner

*Primary Examiner* — John S Kenyon
(74) *Attorney, Agent, or Firm* — W&C IP

(57) ABSTRACT

The present invention relates to highly soluble, non-fluorescent and photostable myosin inhibitors; especially, for in vivo inhibition of the ATPase activity of neuronal non-muscle myosin 2 of formula (II): wherein $Q_1$, $Q_2$, $Q_3$, $Q_4$, $R_1$, $R_2$, $R_4$ and $R_5$ are defined in claim 1. The invention also relates to pharmaceutical compositions or medicaments comprising the compounds of the invention and processes for manufacturing these compounds and their intermediates.

(II)

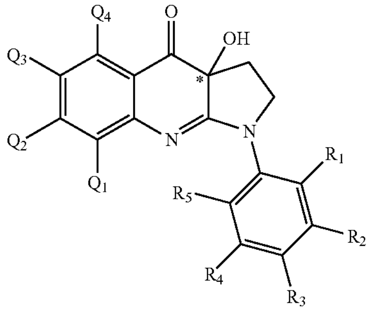

22 Claims, 17 Drawing Sheets

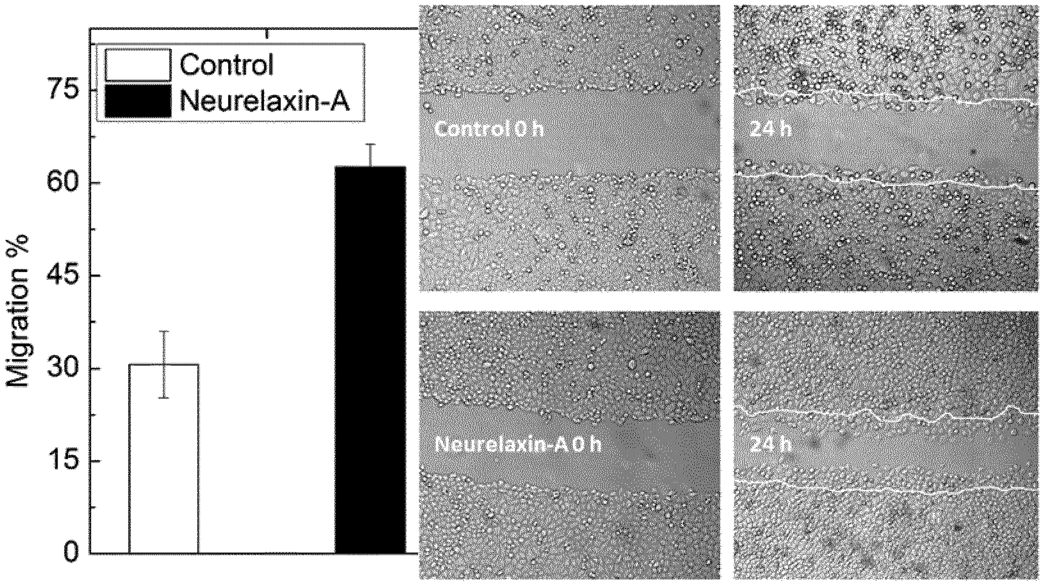
FIG. 3D-E
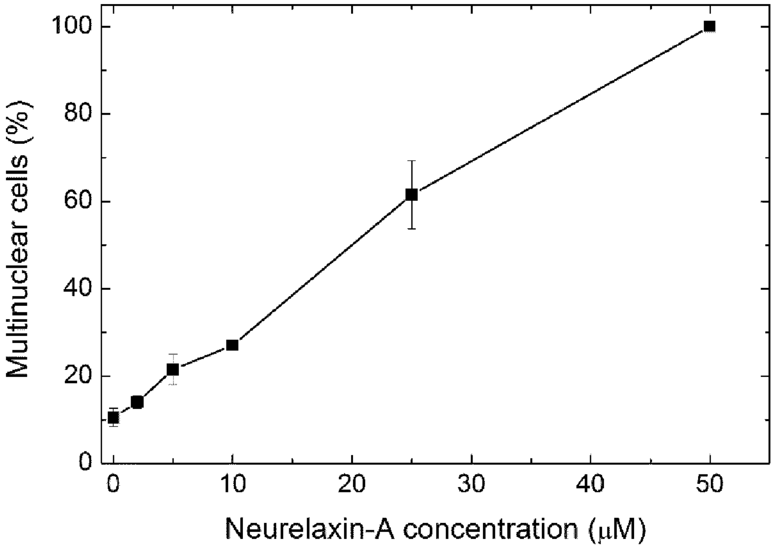
FIG. 3F

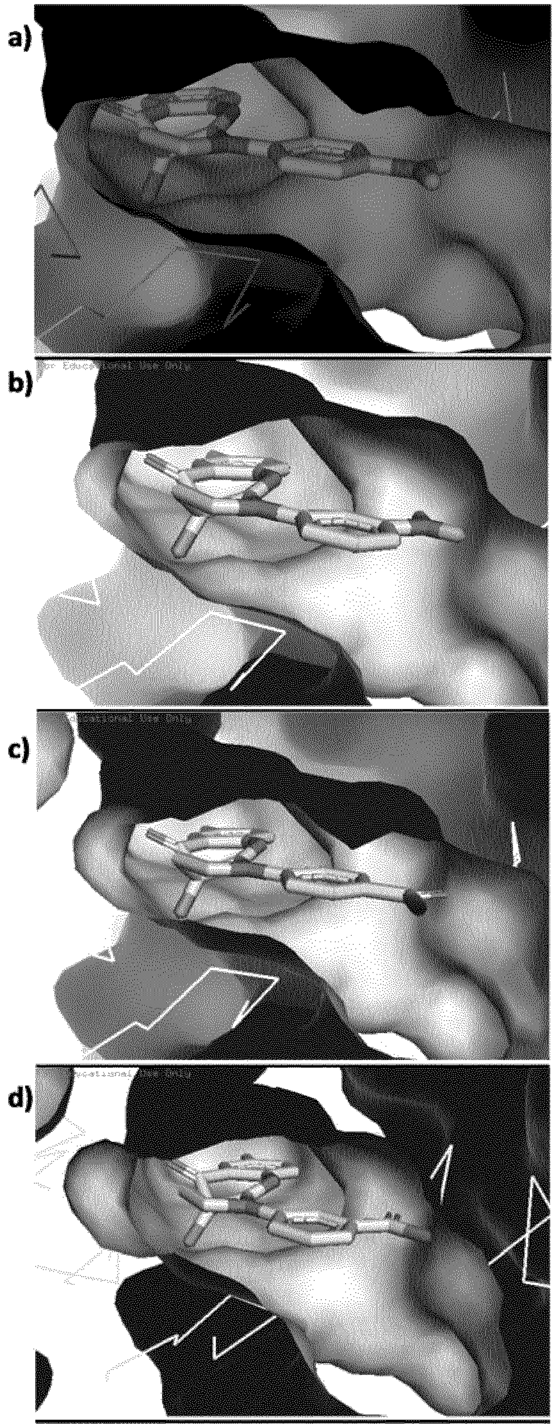
FIG. 9A-D

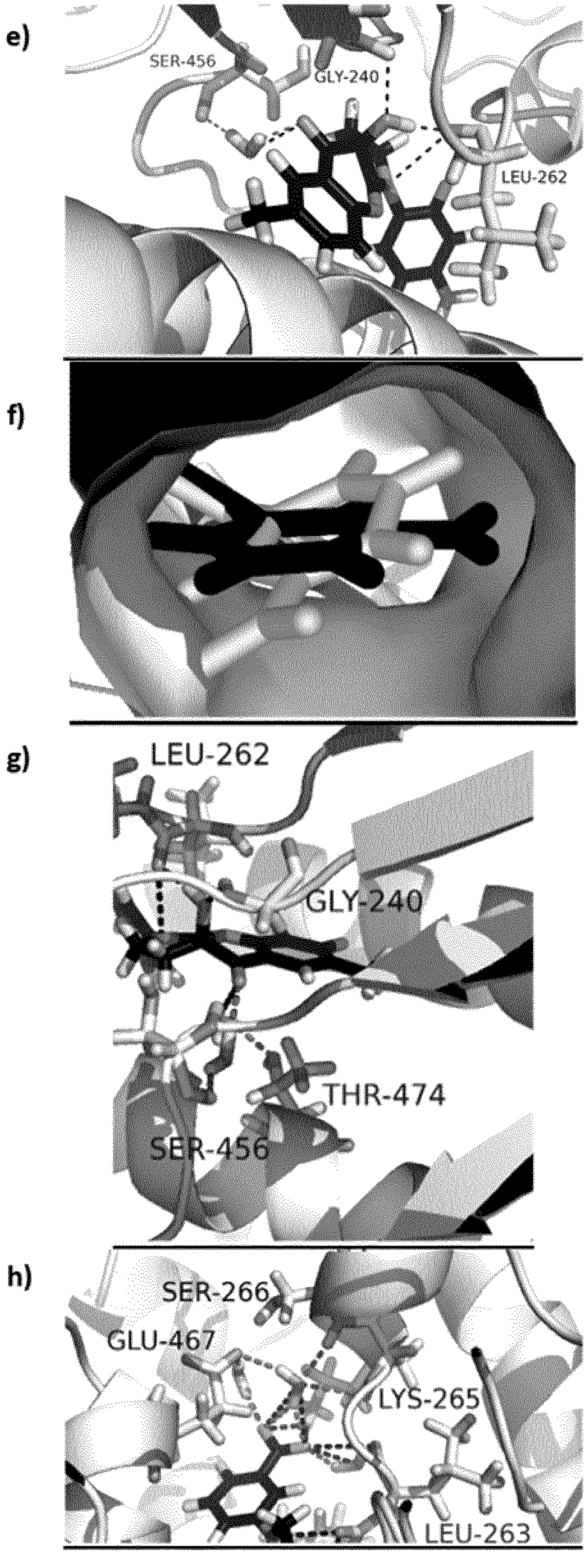
FIG. 9E-H

WATER-SOLUBLE MYOSIN 2 INHIBITORS FOR THE TREATMENT OF NEUROLOGICAL, NEUROPATHIC OR PSYCHIATRIC DISEASES

FIELD OF INVENTION

The present invention relates to highly soluble, non-fluorescent and photostable myosin 2 isoform specific inhibitors; especially, for in vivo inhibition of the ATPase activity of neuronal non-muscle myosin 2 isoforms. These new compounds are also useful as therapeutic compounds, particularly in the treatment and/or prevention of myosin 2 mediated diseases. Particularly, this invention relates to the use of the compounds of the invention for treating neurological, neuropathic and/or psychiatric diseases such as schizophrenia, cerebral ischemia, stroke, neuropathic pain, spinal cord injury, Alzheimer's disease, Parkinson's disease, amyotrophic lateral sclerosis, Huntington disease, addiction, brain cancer and multiple sclerosis. The invention also relates to pharmaceutical compositions or medicaments comprising the compounds of the invention and processes for manufacturing these compounds and their intermediates.

BACKGROUND OF INVENTION

Psychiatric disorders such as depression, anxiety and schizophrenia are leading causes of disability worldwide, and have important societal impact. However, despite major advances in the understanding of the molecular basis of these disorders in recent years, efforts to discover and develop new drugs for neuropsychiatric disorders have been relatively unsuccessful, leading to an increased awareness as to the limits of current mainstream approaches.

Clearly, novel experimental and theoretical approaches are needed in addressing this problem, using new models that are transposable between preclinical and clinical research, as a crucial element for future drug discovery. However, there has been a lack of sufficient translational efforts applying new basic research findings and technology to molecular pharmacology and biological psychiatry, target discovery and validation, and clinical research. Much was learned in recent years about post-receptor signaling mechanisms, regulation of gene expression, epigenetic mechanisms, integrated mechanisms of synaptic plasticity, and the identification of new biomarkers for vulnerability and drug response and resistance by global genomics and proteomics.

However, a considerable amount of current pharmaceutical research is still focused on the stereotypical "receptor-ligand" interaction and, in contrast to other fields such as cancer, much of the psychiatry research in drug companies in the last two decades has been directed towards replication and implementation of already known mechanisms. As a result, most of the "novel" drugs in psychiatry are still compounds that principally are thought to act on neurotransmitter receptors or transporters. It is crucial to intensify the research on novel intracellular targets by seriously analyzing the challenges for target selectivity and compartment specificity, which such compounds might require (Agid et al., How can drug discovery for psychiatric disorders be improved?, Nature Reviews Drug Discovery 6, 189-201, March 2007).

A potential new target for treating connectivity-related neuronal and psychiatric diseases is the actomyosin system, composed of F-actin and non-muscle myosin 2 in neurons. Actomyosin organization has been found to affect cell-migration and differentiation, neuronal development and dendritic spine density and actomyosin contractility was found to have role in cannabinoid-induced neuronal morphology changes, which supports the pivotal role of the actomyosin system in neuronal functions. Especially non-muscle myosin 2 is a potential target as actin is ubiquitous in all cells, which renders it a less attractive target.

Myosins are a large family of molecular motor proteins encompassing 17 classes identified so far. Among them, myosins 2 are ATP driven molecular motors acting in concert with actin to form a contracting actomyosin network and are responsible for various cellular and physiological functions such as muscle contraction, cytokinesis, differentiation, polarization, cell motility and blebbing.

Until now, blebbistatin (Table 1) was a widely used and well characterized small molecular inhibitor of myosins 2. Indeed, blebbistatin blocks myosin heads in a low actin-affinity state allowing preventing the formation of strongly-bound nonfunctional actomyosin complexes, which make blebbistatin a useful tool in the study of muscle physiology and cellular actomyosin networks.

However, blebbistatin has several disadvantageous physico-chemical properties, such as cytotoxicity, phototoxicity photoinstability and high fluorescence and very poor water solubility (above 10 μM concentration, a slow precipitation can be observed). Since the myosin inhibitory constants of blebbistatin are in the same range as its solubility limit, this property may significantly affect the apparent experimental results.

Additionally, blebbistatin's poor water solubility and high fluorescence results in fluorescent aggregates which can become serious obstacles in light scattering or Green Fluorescent Protein (GFP)-based experiments or may damage the vascular system of model animals.

Therefore, there is a need for developing an alternative to blebbistatin. Especially, there is a need for developing a useful tool for in vivo uses.

Current alternative myosin inhibitors (Table 1) are either not efficient enough or easily cross the blood-brain barrier. Consequently, they lead to side effects; in particular, in cardiac muscle or skeletal muscle.

TABLE 1

| Myosin inhibitors. | |
|---|---|
| Blebbistatin | 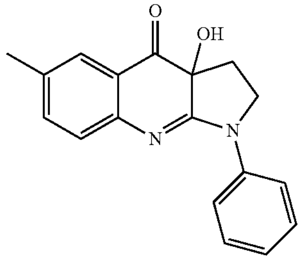 [SMILES: Cc1ccc2c(c1)C(=O)C1(O)CCN(c3ccccc3)C1=N2] |
| Para-nitroblebbistatin | 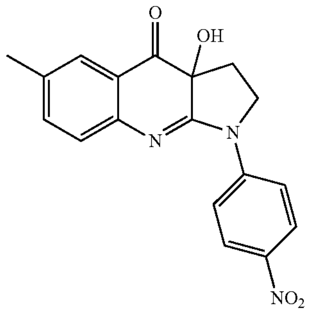 [SMILES: Cc1ccc2c(c1)C(=O)C1(O)CCN(c3ccc([N+](=O)[O-])cc3)C1=N2] |

TABLE 1-continued

| Myosin inhibitors. | |
|---|---|
| Nitroblebbistatin | 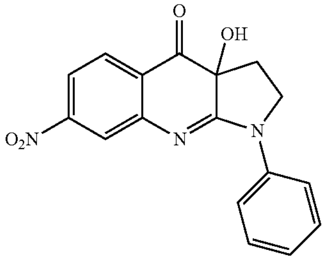 [SMILES: O=C1c2ccc([N+](=O)[O-])cc2N=C2N(c3ccccc3)CCC12O] |

Thus, there also is a need for developing efficient myosin inhibitors as therapeutic agents with reduced, if any, side effects.

Recently, the Applicant has developed a non-fluorescent, photostable, non-cytotoxic and non-phototoxic derivative of blebbistatin named para-nitroblebbistatin, which contains an electron-withdrawing nitro group at the C15 (para) position (Képiró et al., “para-nitroblebbistatin, the non-cytotoxic and photostable myosin 2 inhibitor”, *Angew. Chem. Int. Ed.,* 2014, 53, 1-6).

This compound is a highly specific inhibitor in contrast with the C7 nitro substituted blebbistatin derivative (commonly called nitroblebbistatin, Lucas-Lopez et al., *Organic & Biomolecular Chemistry* 6, No. 12, 2008, 2076) which exerts relatively low affinity to myosin 2 ($IC_{50}$=27.5 μM). Furthermore, the in vitro and in vivo myosin 2 inhibitory properties of para-nitroblebbistatin are not affected by the nitro substitution.

However, despite its highly advantageous properties over blebbistatin, the poor water solubility of para-nitroblebbistatin, similar to blebbistatin, may still restrict its application.

Thus, there is still a need for providing efficient myosin 2 inhibitors with improved physical and chemical properties.

DEFINITIONS

The definitions and explanations below are for the terms as used throughout the entire application, including both the specification and the claims.

When describing the compounds of the invention, the terms used are to be construed in accordance with the following definitions, unless indicated otherwise.

The term “about” preceding a figure means plus or less 10% of the value of said figure.

The term “alkyl” refers to a hydrocarbyl radical of formula $C_nH_{2n+1}$ wherein n is a number greater than or equal to 1. Generally, alkyl groups of this invention comprise from 1 to 20 carbon atoms, preferably from 1 to 10 carbon atoms; more preferably, from 1 to 4 carbon atoms. Alkyl groups may be linear or branched. Suitable alkyl groups include but are not limited to methyl, ethyl, n-propyl, i-propyl, n-butyl, i-butyl, s-butyl; t-butyl, n-pentyl, i-pentyl, s-pentyl and t-pentyl; n-hexyl, i-hexyl, s-hexyl and t-hexyl; heptyl; octyl; nonyl; decyl and undecyl.

The term “heteroalkyl” refers to an alkyl group as defined above, having at least one heteroatom selected from O, N, P or S atom.

The term “halogenoalkyl” refers to an alkyl group as defined above, having at least one halogen. In the present invention, “halogenoalkyl” comprise monohalogenoalkyl or polyhalogenoalkyl.

The term “amino” refers to a $—NH_2$ group or any group derived thereof by substitution of one or two hydrogen atom by an organic aliphatic or aromatic group. Preferably, groups derived from $—NH_2$ are “alkylamino” groups, i.e. N-alkyl groups, comprising monoalkylamino and dialkylamino. The “hydroxylamino” group refers to an amino group substituted by hydroxyl. The “alkylhydroxylamino” group refers to an amino group both substituted by alkyl and hydroxyl.

The term “halogenoheteroalkyl” refers to a heteroalkyl group as defined above, having at least one halogen.

The term “halogenoalkylamino” refers to an alkylamino group as defined above, substituted by at least one halogen.

The term “hydrophilic” refers to any chemical compound having a good affinity for polar solvents, in particular with water or aqueous medium, or with other polar groups.

The term “imido” refers to a $R_1—CO—NR_2—R_3$ group, wherein $R_1$, $R_2$ and $R_3$ may be alkyl group (“alkylimido”) optionally substituted by halogen (“halogenoalkylimido”).

The term “amido” refers to the moieties —CO—NRR' or —NR—CO—R', wherein R and R' represent preferably H, alkyl or aryl. According to a specific embodiment, “amido” refers to the —CO—NH2 moiety. The term “alkylamido” refers to any amido group substituted by at least one alkyl group. The term “halogenoalkylamido” refers to any alkylamido group wherein the alkyl group is substituted by at least one halogen.

The term “nitro” refers to $—NO_2$.

The term “alkoxyl” refers to any group —O-alkyl, wherein alkyl is as defined above. Suitable alkoxy groups include for example methoxy, ethoxy, n-propoxy, isopropoxy, n-butoxy, f-butoxy, sec-butoxy, and n-pentoxy.

The term “carboxyl” refers to —COOH.

The term “ester” refers to —COOR group, wherein R is selected from alkyl or alkene group.

The term “carbonyl” refers to —CO— function. The term “oxycarbonyl” refers to —O—CO— function.

The term “formyl” refers to a —CHO.

The term “halogen” refers to fluoro (F), chloro (CO or bromo (Br) atom.

The term “hydroxyl” refers to —OH.

The term “isostere” refers to atoms, molecules or ions having the same valence (i.e. the identical outer shell of electrons). In the present invention, the terms “carboxylic acid isostere” refers to molecules or ions having the same valence than carboxyl group.

The term “thiol” refers to —SH.

The term “phosphoryl” refers to $—PO_3^{2-}$.

The term “phosphate” refers to $—PO_4^{2-}$.

The term “phosphonic acid” refers to $—PO(OH)_2$.

The term “sulfonyl” refers to $—SO_2—$.

The term “alkylsulfonyl” refers to a sulfonyl group substituted by an alkyl group as defined above. The term “halogenoalkylsulfonyl” refers to an alkylsulfonyl group substituted by halogen.

The term “sulfonate” refers to $—SO_3^-$.

The compounds of formula (I) and subformulae thereof contain a stereogenic carbon center and thus may exist as (R)- and (S)-enantiomers.

The compounds of the invention may be in the form of pharmaceutically acceptable salts. Pharmaceutically acceptable salts of the compounds of the invention include the acid addition and base salts thereof.

Suitable aci578 d addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of the invention may be prepared by one or more of these methods:

(i) by reacting the compound of the invention with the desired acid;

(ii) by reacting the compound of the invention with the desired base;

(iii) by removing an acid- or base-labile protecting group from a suitable precursor of the compound of the invention; or (iv) by converting one salt of the compound of the invention to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a compound in this invention that contains stoichiometric or sub-stoichiometric amounts of one or more pharmaceutically acceptable solvent molecules.

By "charged groups", it is meant any functional group that comprises a residual electronic charge; i.e. any cationic or an anionic group.

All references to compounds of formula (I) include references to solvates, multi-component complexes and liquid crystals thereof.

The compounds of the invention include compounds of formula (I) as hereinbefore defined, including all polymorphs and crystal habits thereof, predrugs and prodrugs thereof and isotopically-labeled compounds of formula (I).

The invention also generally covers all pharmaceutically acceptable predrugs and prodrugs of the compounds of formula (I).

The term "prodrug" as used herein means the pharmacologically acceptable derivatives of compounds of formula (I), such as for example esters, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. myosin 2 inhibitor) that is sufficient to achieve the desired therapeutic or prophylactic effect in the patient to which/whom it is administered.

The term "administration", or a variant thereof (e.g. "administering"), means providing the active agent or active ingredient (e.g. myosin 2 inhibitor), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "myosin 2 mediated disease" as used herein means a disease or a condition which is exacerbated by, or caused by, excessive, inappropriate or unregulated myosin 2 activity. The term "myosin 2 mediated disease" includes all medical conditions alleviated by treatment with a myosin 2 agonist and includes all disease states and/or conditions that are acknowledged now, or that will be found in the future, to be associated with myosin 2 activity. Examples of such diseases in a subject include but are not limited to neuropsychiatric diseases, neurological diseases, neuropathic diseases, muscle diseases, metabolic diseases, viral infections or cancer.

DETAILED DESCRIPTION

Compounds

As noted above, the invention relates to a compound of general formula (I):

(I)

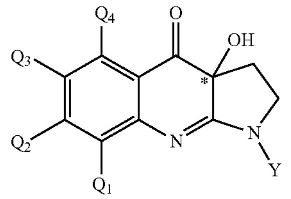

and pharmaceutically acceptable salts and/or solvates thereof, wherein:

$Q_1$, $Q_2$, $Q_3$ and $Q_4$ are each independently selected from H, halogen, alkyl, heteroalkyl, halogenoalkyl, halogenoheteroalkyl, nitro, hydroxyl, thiol and alkoxy;

Y is a hydrophilic moiety; preferably, an aryl or heteroaryl group substituted by at least one hydrophilic group; more preferably, an aryl or heteroaryl group substituted by at least one hydrophilic group selected from phosphonic acid, phosphoryl, hydroxyl, amino, carboxyl and ester having a C1-C4 alkyl chain; and

* stands for the (R)-enantiomer, the (S)-enantiomer, the racemate or the non-racemic mixture of (R) and (S) enantiomers of the corresponding formula (I).

In one embodiment, Y is a hydrophilic moiety; preferably, an aryl or heteroaryl group substituted by at least one hydrophilic group; more preferably, an aryl or heteroaryl group substituted by at least one hydrophilic group selected from hydroxyl, amino, carboxyl and ester having a C1-C4 alkyl chain. In one embodiment, Y is an aryl or heteroaryl group substituted by at least one phosphoryl group. In one embodiment, Y is an aryl or heteroaryl group substituted by at least one phosphonic acid group.

In one embodiment, Y is an aryl or heteroaryl group, substituted or not. In one embodiment, Y is an aryl or heteroaryl group, optionally substituted by phosphonic acid, phosphoryl, halogen, alkyl, heteroalkyl, halogenoalkyl, halogenoheteroalkyl, hydroxyl, nitro, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl or carboxylic acid isostere or any charged groups thereof.

In the present invention, phosphonic acid charged groups include phosphoryl group.

In one embodiment, Y is an aryl or heteroaryl group, optionally substituted by halogen, alkyl, heteroalkyl, halogenoalkyl, halogenoheteroalkyl, hydroxyl, nitro, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl or carboxylic acid isostere or any charged groups thereof.

In one embodiment, carboxylic acid isostere is selected from:

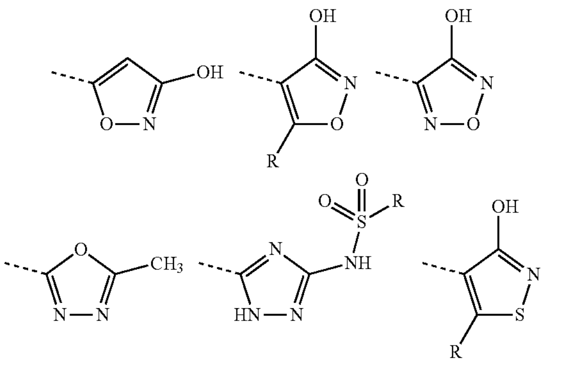

-continued

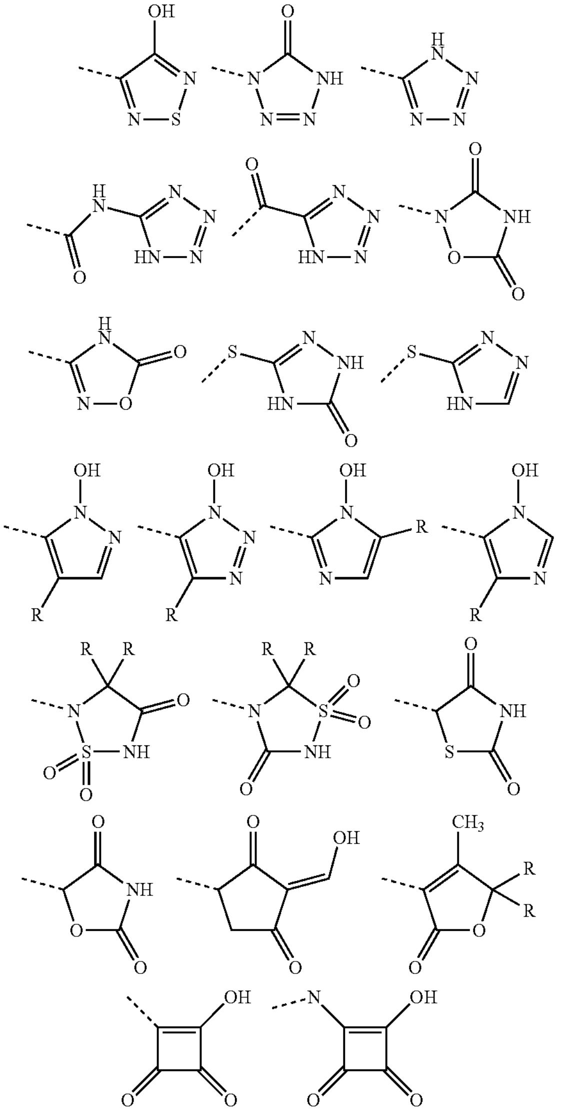

wherein R is selected from hydrogen, alkyl, halogenoalkyl, hydroxyl, thiol, alkoxy, halogenoalkyl, heteroalkyl, halogenoheteroalkyl, sulfonyl, alkylsulfonyl, halogenoalkylsulfonyl, aminosulfonyl, alkylaminosulfonyl, halogenoalkylaminosulfonyl, amidosulfonyl, alkylamidosulfonyl, halogenoalkylamidosulfonyl, formyl, alkylcarbonyl, halogenoalkylcarbonyl alkyloxycarbonyl, halogenoalkyloxycarbonyl, carboxyl and phosphoryl; and represents the point of attachment of the moiety to the rest of the molecule.

In one embodiment, Y is a heteroaryl group selected from:

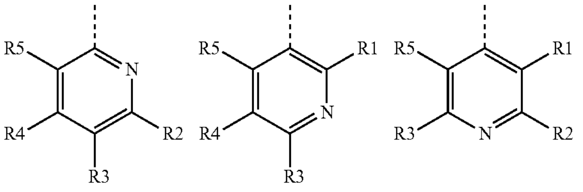

-continued

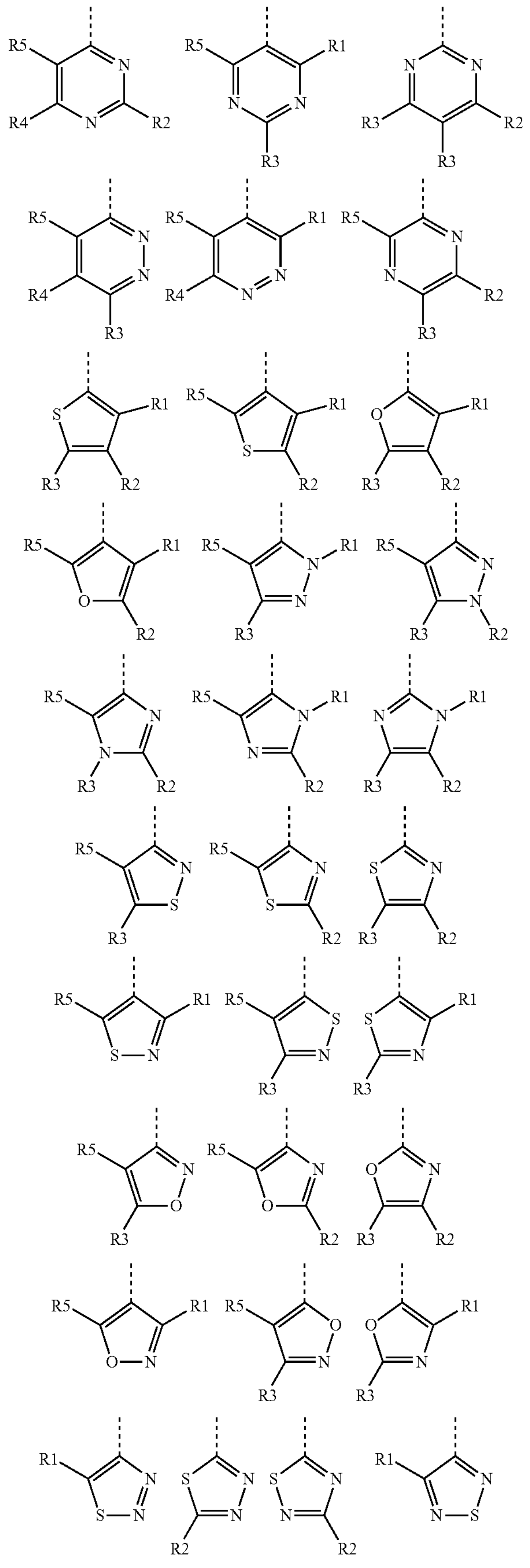

-continued

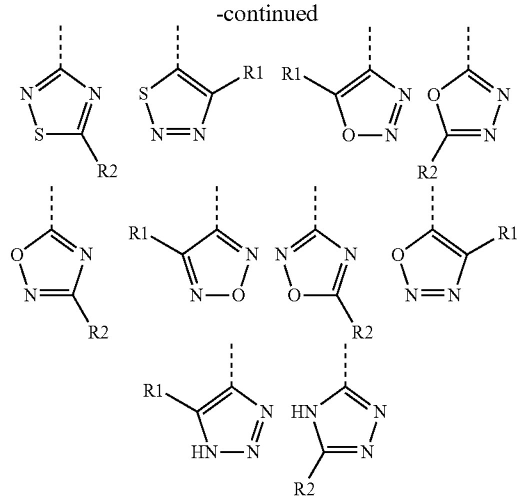

wherein $R_1$, $R_2$, $R_3$, $R_4$ and $R_5$ are each independently selected from hydrogen, halogen, alkyl, heteroalkyl, halogenoalkyl, halogenoheteroalkyl, hydroxyl, nitro, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl and carboxylic acid isostere.

In one embodiment, at least one of $R_1$, $R_2$, $R_3$, $R_4$ and $R_5$ is a hydrophilic group selected from phosphonic acid, phosphoryl, hydroxyl, amino, carboxyl and ester having a C1-C4 alkyl chain or any charged groups thereof. In one embodiment, at least one of $R_1$, $R_2$, $R_3$, $R_4$ and $R_5$ is a phosphonic acid group. In one embodiment, at least one of $R_1$, $R_2$, $R_3$, $R_4$ and $R_5$ is a phosphoryl group. In one embodiment, at least one of $R_1$, $R_2$, $R_3$, $R_4$ and $R_5$ is a hydrophilic group selected from hydroxyl, amino, carboxyl and ester having a C1-C4 alkyl chain or any charged groups thereof.

In one preferred embodiment, $R_1$ and $R_5$ are each independently selected from hydrogen, halogen, nitro, alkyl, alkoxy or heteroalkyl. In one preferred embodiment, $R_1$ and $R_5$ are each independently selected from hydrogen, halogen, nitro, C1-C4 linear or branched alkyl chain, alkoxy or heteroalkyl.

According to one embodiment, preferred compounds of formula (I) are compounds of formula (II):

(II)

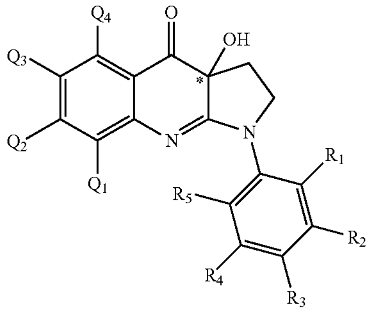

and pharmaceutically acceptable salts and/or solvates thereof, wherein $Q_1$, $Q_2$, $Q_3$ and $Q_4$ are as defined in formula (I);

$R_1$, $R_2$, $R_3$, $R_4$ and $R_5$ are each independently selected from phosphonic acid, phosphoryl, hydrogen, halogen, alkyl, heteroalkyl, halogenoalkyl, halogenoheteroalkyl, hydroxyl, nitro, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl and carboxylic acid isostere; and

* stands for the (R)-enantiomer, the (S)-enantiomer, the racemate or the non-racemic mixture of (R) and (S) enantiomers of the corresponding formula (II).

In one embodiment, $R_1$, $R_2$, $R_3$, $R_4$ and $R_5$ are each independently selected from hydrogen, halogen, alkyl, heteroalkyl, halogenoalkyl, halogenoheteroalkyl, hydroxyl, nitro, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl and carboxylic acid isostere.

In one embodiment, preferred compounds of formula (II) are compounds wherein:

$Q_1$, $Q_2$, $Q_3$ and $Q_4$ are as defined in formula (I);

$R_1$, $R_2$, $R_3$, $R_4$ and $R_5$ are as defined in formula (II);

wherein at least one of $R_2$, $R_3$ and $R_4$ are a hydrophilic group selected from phosphonic acid, phosphoryl, hydroxyl, amino, carboxyl and ester having a $C_1$-$C_4$ alkyl chain or any charged groups thereof; and

* stands for the (R)-enantiomer, the (S)-enantiomer, the racemate or the non-racemic mixture of (R) and (S) enantiomers of the corresponding formula (II).

In one embodiment, preferred compounds of formula (II) are compounds wherein:

$Q_1$, $Q_2$, $Q_3$ and $Q_4$ are as defined in formula (I);

$R_1$, $R_2$, $R_3$, $R_4$ and $R_5$ are as defined in formula (II);

wherein at least one of $R_2$, $R_3$ and $R_4$ are a hydrophilic group selected from hydroxyl, amino, carboxyl and ester having a C1-C4 alkyl chain or any charged groups thereof; and

* stands for the (R)-enantiomer, the (S)-enantiomer, the racemate or the non-racemic mixture of (R) and (S) enantiomers of the corresponding formula (II).

In one embodiment, preferred compounds of formula (II) are compounds wherein:

$Q_1$, $Q_2$, $Q_3$ and $Q_4$ are as defined in formula (I);

$R_1$, $R_2$, $R_3$, $R_4$ and $R_5$ are as defined in formula (II);

wherein at least one of $R_2$, $R_3$ and $R_4$ are a hydrophilic group selected from hydroxyl, amino, carboxyl and ester having a C1-C4 alkyl chain or any charged groups thereof; and

* stands for the (R)-enantiomer, the (S)-enantiomer, the racemate or the non-racemic mixture of (R) and (S) enantiomers of the corresponding formula (II);

provided that:

when $Q_3$ is methyl, then $R_3$ is not chosen among hydrogen, nitro, and chloro;

when $Q_3$ is methyl and $Q_1$, $Q_2$, $Q_4$, $R_1$, $R_2$, $R_4$ and $R_5$ are hydrogen, then $R_3$ is not chosen among hydrogen, nitro, and chloro;

when $Q_1$, $Q_2$, $Q_4$, $R_1$, $R_2$, $R_3$, $R_4$ and $R_5$ are hydrogen, then $Q_2$ is not nitro.

In one embodiment, preferred compound of Formula (II) is the (S)-enantiomer.

In one embodiment, preferred compound of Formula (II) is compound wherein $Q_3$ is methyl and $Q_1$, $Q_2$, $Q_4$, $R_1$, $R_2$, $R_4$ and $R_5$ are hydrogen; and $R_3$ is a hydrophilic group selected from phosphonic acid, phosphoryl, hydroxyl, amino, carboxyl and ester having a C1-C4 alkyl chain.

In one embodiment, preferred compound of Formula (II) is compound wherein $Q_3$ is methyl and $Q_1$, $Q_2$, $Q_4$, $R_1$, $R_2$, $R_4$ and $R_5$ are hydrogen; and $R_3$ is a hydrophilic group selected from hydroxyl, amino, carboxyl and ester having a C1-C4 alkyl chain.

In one embodiment, preferred compounds of Formula (II) are compounds of general formula (II bis):

(II bis)

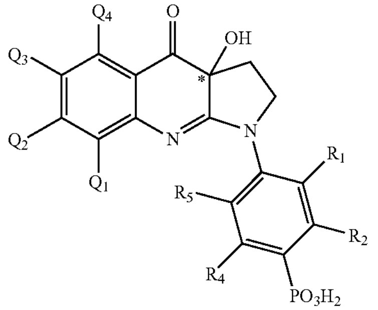

and pharmaceutically acceptable salts and/or solvates thereof, wherein $Q_1$, $Q_2$, $Q_3$, $Q_4$, $R_1$, $R_2$, $R_4$ and $R_5$ are as defined in formula (II).

In one embodiment, preferred compounds of Formula (II) are compounds of general formula (II ter):

(II ter)

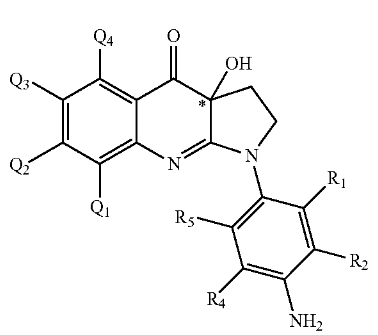

and pharmaceutically acceptable salts and/or solvates thereof, wherein $Q_1$, $Q_2$, $Q_3$, $Q_4$, $R_1$, $R_2$, $R_4$ and $R_5$ are as defined in formula (II).

In one embodiment, preferred compounds of Formula (II) are compounds of general formula (III):

(III)

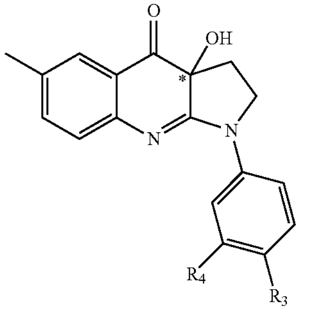

and pharmaceutically acceptable salts and/or solvates thereof, wherein:

$R_3$ and $R_4$ are each independently selected from phosphonic acid, phosphoryl, hydrogen, halogen, alkyl, heteroalkyl, halogenoalkyl, halogenoheteroalkyl, hydroxyl, nitro, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl and carboxylic acid isostere or any charged groups thereof; and

* stands for the (R)-enantiomer, the (S)-enantiomer, the racemate or the non-racemic mixture of (R) and (S) enantiomers of the corresponding formula (III).

In one embodiment, $R_3$ and $R_4$ are each independently selected from hydrogen, halogen, alkyl, heteroalkyl, halogenoalkyl, halogenoheteroalkyl, hydroxyl, nitro, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl and carboxylic acid isostere or any charged groups thereof.

In one embodiment, at least one of $R_3$ and $R_4$ is selected from a hydrophilic group; preferably, a hydrophilic group selected from phosphonic acid, phosphoryl, hydroxyl, amino, carboxyl and ester having a C1-C4 alkyl chain. In one embodiment, at least one of $R_3$ and $R_4$ is selected from a hydrophilic group; preferably, a hydrophilic group selected from hydroxyl, amino, carboxyl and ester having a C1-C4 alkyl chain.

In one embodiment, preferred compounds of Formula (III) are compounds wherein:

$R_3$ and $R_4$ are as defined in formula (III);

at least one of $R_3$ and $R_4$ is selected from a hydrophilic group; preferably, a hydrophilic group selected from phosphonic acid, phosphoryl, hydroxyl, amino, carboxyl and ester having a C1-C4 alkyl chain or any charged groups thereof; and

* stands for the (R)-enantiomer, the (S)-enantiomer, the racemate or the non-racemic mixture of (R) and (S) enantiomers of the corresponding formula (III);

provided that when $R_4$ is hydrogen, $R_3$ is not hydrogen, nitro or chloro.

In one embodiment, preferred compounds of Formula (III) are compounds wherein:

$R_3$ and $R_4$ are as defined in formula (III);

at least one of $R_3$ and $R_4$ is selected from a hydrophilic group; preferably, a hydrophilic group selected from hydroxyl, amino, carboxyl and ester having a C1-C4 alkyl chain or any charged groups thereof; and

* stands for the (R)-enantiomer, the (S)-enantiomer, the racemate or the non-racemic mixture of (R) and (S) enantiomers of the corresponding formula (III);

provided that when $R_4$ is hydrogen, $R_3$ is not hydrogen, nitro or chloro.

In one embodiment, compounds of Formula (III) do not comprise compounds wherein $R_3$ is halogen and $R_4$ is hydrogen. In one embodiment, compounds of Formula (III) do not comprise compounds wherein $R_3$ is chlorine (—Cl) and $R_4$ is hydrogen. In one embodiment, compounds of Formula (III) do not comprise compounds wherein $R_3$ is iodine (—I) and $R_4$ is hydrogen. In one embodiment, compounds of Formula (III) do not comprise compounds wherein $R_3$ is bromine (—Br) and $R_4$ is hydrogen. In one embodiment, compounds of Formula (III) do not comprise compounds wherein $R_3$ is fluorine (—F) and $R_4$ is hydrogen.

In one embodiment, compound of Formula (III) is not blebbistatin (CAS 856925-71-8). In one embodiment, compound of Formula (III) is not para-nitroblebbistatin. In one embodiment, compound of Formula (III) is not para-chloroblebbistatin.

In one specific embodiment, compound of formula (III) is the (R)-enantiomer. In one embodiment, compound of formula (III) is the (S)-enantiomer. In one embodiment, compound of formula (III) is the racemate. In one embodiment, compound of formula (III) is the non-racemic mixture of (R) and (S) enantiomers.

In one embodiment, preferred compounds of formula (III) are selected from those wherein:

$R_3$ is $NH_2$ and $R_4$ is H;

$R_3$ is $PO_3H_2$ and $R_4$ is H;

$R_3$ is H and $R_4$ is COOH;

$R_3$ is COOH and $R_4$ is H;

$R_3$ is H and $R_4$ is OH; or $R_3$ is OH and $R_4$ is H.

According to one embodiment, preferred compounds of Formula (III) are those of Formula (IV):

(IV)

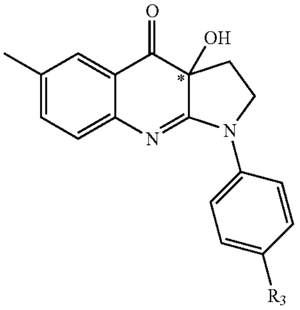

and pharmaceutically acceptable salts and/or solvates thereof, wherein: $R_3$ is selected from phosphonic acid, phosphoryl, heteroalkyl, halogenoheteroalkyl, hydroxyl, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl and carboxylic acid isostere; preferably, $R_3$ is selected from formyl, carboxyl, ester, alkoxy, amino, alkylamino, hydroxyl or any charged group thereof; more preferably, $R_3$ is selected from carboxyl, ester, hydroxyl, amino or any charged group thereof; and

* stands for the (R)-enantiomer, the (S)-enantiomer, the racemate or the non-racemic mixture of (R) and (S) enantiomers of the corresponding formula (IV).

In one embodiment, $R_3$ is a hydrophilic group; preferably, a hydrophilic group selected from hydroxyl, amino, carboxyl and ester having a C1-C4 alkyl chain or any charged groups thereof.

In one embodiment, $R_3$ is selected from heteroalkyl, halogenoheteroalkyl, hydroxyl, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl and carboxylic acid isostere; preferably, $R_3$ is selected from formyl, carboxyl, ester, alkoxy, amino, alkylamino, hydroxyl or any charged group thereof; more preferably, $R_3$ is selected from carboxyl, ester, hydroxyl, amino or any charged group thereof.

In one embodiment, $R_3$ is not chloro.

In one specific embodiment, compound of formula (IV) is the (R)-enantiomer. In one embodiment, compound of formula (IV) is the (S)-enantiomer. In one embodiment, compound of formula (IV) is the racemate. In one embodiment, compound of formula (IV) is the non-racemic mixture of (R) and (S) enantiomers.

Particularly preferred compounds of formula (I) of the invention are those listed in Table 2 hereafter.

TABLE 2

| Cpd no | Structure | Chemical name |
|---|---|---|
| 1 | 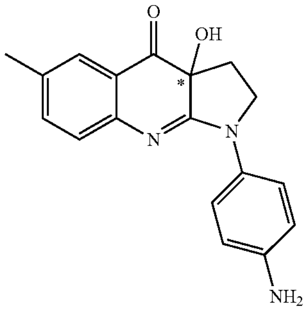 | 1-(4-aminophenyl)-3a-hydroxy-6-methyl-3,3a-dihydro-1H-pyrrolo[2,3-b]quinolin-4(2H)-one or neurelaxin-A |
| 2 | 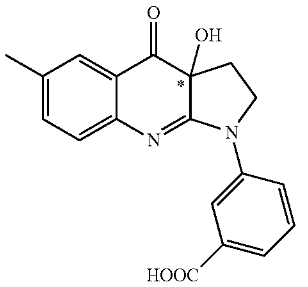 [SMILES: Cc1ccc2c(c1)C(=O)C1(O)CCN(c3cccc(C(=O)O)c3)C1=N2] | 3-(3a-hydroxy-6-methyl-4-oxo-2,3,3a,4-tetrahydro-1H-pyrrolo[2,3-b]quinolin-1-yl) benzoic acid |

TABLE 2-continued

| Cpd no | Structure | Chemical name |
|---|---|---|
| 3 | 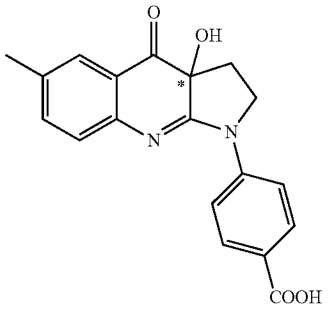 [SMILES: Cc1ccc2c(c1)C(=O)C1(O)CCN(c3ccc(C(=O)O)cc3)C1=N2] | 4-(3a-hydroxy-6-methyl-4-oxo-2,3,3a,4-tetrahydro-1H-pyrrolo[2,3-b]quinolin-1-yl) benzoic acid |
| 4 | 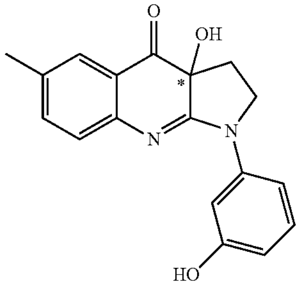 [SMILES: Cc1ccc2c(c1)C(=O)C1(O)CCN(c3cccc(O)c3)C1=N2] | 3a-hydroxy-1-(3-hydroxyphenyl)-6-methyl-3,3a-dihydro-1H-pyrrolo[2,3-b]quinolin-4(2H)-one |
| 5 | 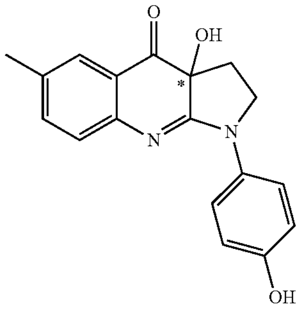 [SMILES: Cc1ccc2c(c1)C(=O)C1(O)CCN(c3ccc(O)cc3)C1=N2] | 3a-hydroxy-1-(4-hydroxyphenyl)-6-methyl-3,3a-dihydro-1H-pyrrolo[2,3-b]quinolin-4(2H)-one |
| 6 | 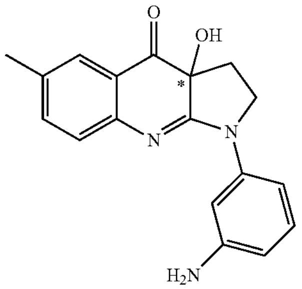 [SMILES: Cc1ccc2c(c1)C(=O)C1(O)CCN(c3cccc(N)c3)C1=N2] | 1-(3-aminophenyl)-3a-hydroxy-6-methyl-3,3a-dihydro-1H-pyrrolo[2,3-b]quinolin-4(2H)-one |
| 7 | 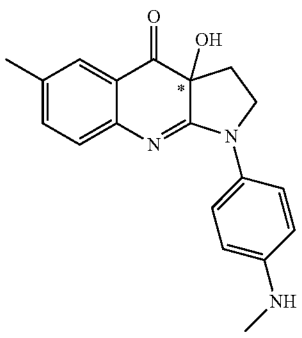 [SMILES: CNc1ccc(N2CCC3(O)C(=O)c4cc(C)ccc4N=C23)cc1] | 3a-hydroxy-6-methyl-1-(4-(methylamino)phenyl)-3,3a-dihydro-1H-pyrrolo[2,3-b]quinolin-4(2H)-one |

TABLE 2-continued

| Cpd no | Structure | Chemical name |
|---|---|---|
| 8 | 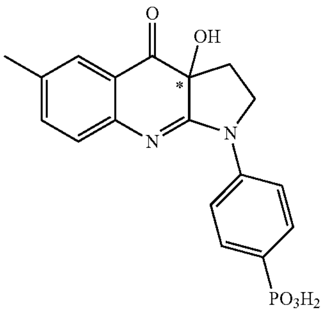 | (4-(3a-hydroxy-6-methyl-4-oxo-2,3,3a,4-tetrahydro-1H-pyrrolo[2,3-b] quinolin-1-yl) phenyl) phosphonic acid |

and pharmaceutically acceptable salts and/or solvates thereof.

In Table 1, the term "Cpd" means compound.

The compounds of Table 1 were named using ChemBioDraw® Ultra version 12.0 (PerkinElmer).

In one embodiment, preferred compounds are selected from:

1-(4-aminophenyl)-3a-hydroxy-6-methyl-3,3a-dihydro-1H-pyrrolo[2,3-b]quinolin-4(2H)-one;

3-(3a-hydroxy-6-methyl-4-oxo-2,3,3a,4-tetrahydro-1H-pyrrolo[2,3-b]quinolin-1-yl)benzoic acid;

4-(3a-hydroxy-6-methyl-4-oxo-2,3,3a,4-tetrahydro-1H-pyrrolo[2,3-b]quinolin-1-yl)benzoic acid;

3a-hydroxy-1-(3-hydroxyphenyl)-6-methyl-3,3a-dihydro-1H-pyrrolo[2,3-b]quinolin-4(2H)-one;

3a-hydroxy-1-(4-hydroxyphenyl)-6-methyl-3,3a-dihydro-1H-pyrrolo[2,3-b]quinolin-4(2H)-one; and 1-(3-aminophenyl)-3a-hydroxy-6-methyl-3,3a-dihydro-1H-pyrrolo[2,3-b]quinolin-4(2H)-one.

In one embodiment, preferred compound is (4-(3a-hydroxy-6-methyl-4-oxo-2,3,3a,4-tetrahydro-1H-pyrrolo[2,3-b]quinolin-1-yl)phenyl)phosphonic acid.

In one embodiment, preferred compound is (4-[(3aS)-3a-hydroxy-6-methyl-4-oxo-1H,2H,3H,3aH,4H-pyrrolo[2,3-b]quinolin-1-yl]phenyl) phosphonic acid.

Advantageously, compounds of the invention as defined above are water-soluble, non-fluorescent and photostable compounds. In one embodiment, compounds of the invention as defined above are water-soluble, non-fluorescent and photostable compounds in vitro and in vivo.

Uses

The invention also relates to a composition, a pharmaceutical composition or a medicament comprising at least one compound of the invention as defined above, or a pharmaceutically acceptable salt and/or solvate thereof.

According to one embodiment, the composition comprises at least one compound of the invention as defined above.

According to another embodiment, the pharmaceutical composition or the medicament comprises a compound of the invention as defined above or a pharmaceutically acceptable salt and/or solvate thereof, and at least one pharmaceutically acceptable carrier, diluent, excipient and/or adjuvant.

In one embodiment, the pharmaceutical composition or the medicament further comprises additional therapeutic agents and/or active ingredients.

In one embodiment, the pharmaceutical composition or the medicament comprises a compound of Formula (I). In one embodiment, the pharmaceutical composition or the medicament comprises a compound of Formula (II). In one embodiment, the pharmaceutical composition or the medicament comprises a compound of Formula (III). In one embodiment, the pharmaceutical composition or the medicament comprises a compound of Formula (IV).

In one embodiment, the pharmaceutical composition or the medicament comprises 1-(4-aminophenyl)-3a-hydroxy-6-methyl-3,3a-dihydro-1H-pyrrolo[2,3-b]quinolin-4(2H)-one (also called neurelaxin-A or compound 1).

In one embodiment, the pharmaceutical composition or the medicament comprises (4-(3a-hydroxy-6-methyl-4-oxo-2,3,3a,4-tetrahydro-1H-pyrrolo[2,3-b]quinolin-1-yl)phenyl) phosphonic acid (compound 8).

Compound for Use

The invention further provides the use of compounds of the invention or a pharmaceutically acceptable salt and/or solvate thereof. Especially, the compounds of the invention are useful as medicaments in the prevention and/or the treatment of myosin 2 mediated diseases. In one embodiment, the compounds of the invention are useful as medicaments in the prevention and/or the treatment of non-muscle myosin 2 mediated diseases.

The compounds of the invention are therefore useful as medicaments, in particular in the prevention and/or treatment of neurological, neuropathic and/or psychiatric disease or trauma such as, but not limited to, schizophrenia, depression, obsessive-compulsive disorder, drug addiction, visual hallucination, auditory hallucination, eating disorder, bipolar disorder, Alzheimer's disease, brain ischemia, cerebellar ataxia, cerebrovascular accident, movement disorders, corticobasal ganglionic degeneration, Creutzfeldt-Jakob syndrome, Dandy-Walker syndrome, dementia, encephalitis, encephalomyelitis, epilepsy, Hallervorden-Spatz syndrome, Huntington disease, Hydrocephalus, ischemic attack, lacunar syndromes, Landau-Kleffner syndrome, Lewy Body disease, Machado-Joseph disease, Meige syndrome, meningitis, multiple system atrophy, neuroaxonal dystrophies, Parkinsonian disorders, Shy-Drager syndrome, spinocerebellar ataxias, spinocerebellar degenerations, Tourette syndrome.

In one preferred embodiment, the myosin 2 mediated disease is selected from schizophrenia, cerebral ischemia, stroke, neuropathic pain, spinal cord injury, Alzheimer's disease, Parkinson's disease, addiction, brain cancer and multiple sclerosis.

In one preferred embodiment, the myosin 2 mediated disease is selected from cerebral ischemia and spinal cord injury.

In one preferred embodiment, the compound of invention inhibits the effects of cannabinoid receptors activation (CB1R and CB2R).

In one embodiment, the compounds of the invention are useful for inhibition of cytokinesis. In one embodiment, the EC50 values of the inhibition of cytokinesis for compounds of the invention range from 13 μM to 25 μM, preferably is about 17.8 μM.

The compounds of the invention are therefore useful as medicaments, in particular in the prevention and/or treatment of cancer such as, but not limited to, tumor, metastasis, brain cancer, astrocytoma, glioblastoma, lymphoma of the brain, neuroblastoma, spinal cord tumors including lymphoma, astrocytoma, glioma, meningioma, and metastases of the spinal cord. In one embodiment, the compounds of the invention are useful in the prevention of central nervous system disorders and/or degenerative conditions.

In one embodiment, the compounds of the invention are useful in axonal growth and regeneration. In one embodiment, the compounds of the invention are useful as medicaments in the prevention and/or the treatment of neuron and/or axon loss. In one embodiment, the compounds of the invention are useful for promoting axonal growth.

In one preferred embodiment, the compounds of the invention improves oxidative stress resistance of neurons.

In one embodiment, the compounds of the invention are useful as medicaments, in particular for the protection of axons, especially from RhoA/ROCK mediated growth cone collapse. The term "RhoA" means Ras homolog gene family (Rho), member A and the term "ROCK" refers to Rho-associated proteins kinase.

In one embodiment, the compounds of the invention are useful as medicaments, in particular in the prevention and/or treatment of demyelination, preferably demyelination of axons. In one embodiment, the compounds of the invention are useful for improving myelination.

In one embodiment, the compounds of the invention are useful for improving synaptic function, memory and/or learning.

In one embodiment, the compounds of the invention have neuroprotective properties.

Preferably, the patient is a warm-blooded animal, more preferably a human.

In a specific embodiment, the compounds of the invention are especially useful in the treatment and/or prevention of schizophrenia.

In a specific embodiment, the compound of the invention inhibits the neuronal actomyosin contractility. In a specific embodiment, the compound of general formula (II) inhibits neuronal actomyosin contractility, preferably inhibits neuronal actomyosin contractility in vivo.

In a specific embodiment, the compound of the invention specifically inhibits skeletal muscle myosin. In one embodiment, the EC50 values of the inhibition of the maximal angular velocity by the compound of the invention range from more than 0 μM to 2 μM.

In a specific embodiment, the compound of the invention specifically inhibits *Dictyostelium* myosin.

The invention further provides the use of compounds of the invention or a pharmaceutically acceptable solvate thereof for the manufacture of a medicament for treating and/or preventing myosin 2-mediated diseases.

According to a further feature of the present invention there is a method provided for modulating myosin 2 activity, in a patient, preferably a warm blooded animal, and even more preferably a human, in need of such treatment, which comprises administering to said patient an effective amount of compound of the present invention, or a pharmaceutically acceptable salt and/or solvate thereof.

According to one embodiment, the compounds of the invention and their pharmaceutically acceptable salts and/or solvates, respectively, may be administered as part of a combination therapy. Thus, are included within the scope of the present invention embodiments comprising co-administration of, and compositions and medicaments which contain, in addition to a compound of the present invention, a pharmaceutically acceptable solvate thereof as active ingredient, additional therapeutic agents and/or active ingredients. Such multiple drug regimens, often referred to as "combination therapy", may be used in the treatment and/or prevention of any of the diseases or conditions mediated by or associated with myosin 2 activity modulation. The use of such combinations of therapeutic agents is especially pertinent with respect to the treatment of the above-mentioned disorders within a patient in need of treatment or one at risk of becoming such a patient.

In one embodiment, the compound of the invention as defined above, inhibits from more than 0% to 100% of the myosin 2 activity; preferably from 50% to 100%; even more preferably from 80% to 100% of the myosin 2 activity. In one embodiment, the compound of the invention as defined above, totally inhibits the myosin 2 activity. Methods for measuring the myosin 2 activity are well-known from the skilled artisan. An example of such a method is disclosed in the Examples. Briefly, said method includes binding assays to the allosteric pocket of myosins, structural assays, conformational assays, and biological activity assays.

Technics for determining binding are well known in the art and include assays based on fluorescence such as fluorescence resonance energy transfer (FRET) assays and fluorescence polarization (FP) assays, immunological assays such as ELISA, surface plasmon resonance, isothermal titration calorimetry and Fourier Transformed Infrared Spectroscopy (FTIR).

Structural assays conformation may be determined by using methods known in the art including X-ray crystallography and/or NMR spectroscopy.

A change in conformation may be determined by using methods known in the art including the determination of electrophoretic or chromatographic mobility and fluorescence-based methods. In the latter case, changes in intramolecular distances between fluorophores arising from a change of conformation may be determined.

Biological activity assays may be determined by using methods known in the art including ATPase assays.

In one embodiment, the pharmaceutical composition or medicament comprising the compound of the invention, may be in a form suitable for intracranial administration, oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person.

In one preferred embodiment, the compounds of the invention and their pharmaceutically acceptable salts and/or solvates, respectively, may be administered by intracranial administration.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

In one embodiment, the pharmaceutical composition or medicament of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Another object of the present invention is a method for inhibiting myosin 2 activity in a subject in need thereof comprising administering a therapeutically effective amount of a compound of the invention (preferably, compounds of formula (III)) to said subject. Another object of the present invention is a method of treatment of central nervous system disorders and/or degenerative conditions.

Another object of the present invention is a method for modulating cell migration (such as cancer cell, leukocyte, macrophages, microglia etc.) in a subject in need thereof comprising administering a therapeutically effective amount of compound of the invention to said subject.

Another object of the present invention is a method for inhibiting cytokinesis in a subject in need thereof comprising administering a therapeutically effective amount of a compound of the invention to said subject.

Another object of the present invention is a method for modulating neuronal remodeling in a subject in need thereof comprising administering a therapeutically effective amount of a compound of the invention to said subject.

Another object of the present invention is a method for promoting neurite growth in a subject in need thereof comprising administering a therapeutically effective amount of a compound of the invention to said subject. In one embodiment, the neurite growth after the treatment with a compound of the invention ranges from more than 0 to 10 μm/min, preferably from 0.1 to 7 μm/min; more preferably is about 1 μm/min.

Another object of the present invention is a method for protecting axons from RhoA/ROCK mediated growth cone collapse.

Another object of the present invention is a method for modulating synaptic plasticity in a subject in need thereof comprising administering a therapeutically effective amount of a compound of the invention to said subject.

Another object of the present invention is a method for improving oxidative stress resistance.

Another object of the present invention is a method for preventing and/or treating demyelination, preferably demyelination of axons. Another object of the present invention is a method for improving myelination.

Another object of the present invention is a method of treatment for neurological, neuropathic or psychiatric disorders; preferably for schizophrenia, cerebral ischemia, stroke, neuropathic pain, spinal cord injury, Alzheimer's disease, Parkinson's disease, addiction, brain cancer and multiple sclerosis; more preferably for cerebral ischemia or spinal cord injury.

Another object of the present invention is a method for improving synaptic stability, memory and/or learning.

Process

The invention also relates to a process for manufacturing the compounds as defined above. Especially, the invention relates to a process comprising at least one a step of mixture of para-nitroblebbistatin with an ammonium compound in a solvent.

In one embodiment, the process further comprises the use of a catalyst; preferably, the catalyst is palladium, preferably black palladium.

In one embodiment, the process is led at room temperature (i.e. about 20° C.). In one embodiment, the process is led during at least 12 hours; preferably, 18 hours.

In one embodiment, the solvent is an alcohol; preferably; the solvent is an aliphatic alcohol; more preferably, the solvent is methanol. In one embodiment, para-nitroblebbistatin is in the solvent at a concentration ranging from more than 0 to 100 mg/ml, preferably from 0.5 mg/ml to 50 mg/ml, preferably from 1 mg/ml to 25 mg/ml, more preferably from 1 mg/ml to 10 mg/ml. In one embodiment, para-nitroblebbistatin is in the solvent at a concentration of about 5 mg/ml. In one embodiment, para-nitroblebbistatin is in the solvent at a concentration of about 2 mg/ml.

In one embodiment, the ammonium compound is ammonium formate.

BRIEF DESCRIPTION OF THE DRAWINGS

FIG. 9 is a set of images presenting the results of in silico simulations with rationally designed derivatives of Neurelaxin-A. Neurelaxin-A (compound 1 in Table 1) and compounds 2, 3, 6 in Table 1 were placed deep into the actin binding cleft, close to the nucleotide binding pocket in NMII myosin crystal structure (PBD ID: 3mjx). (a)-(d) Substitutions at phenyl group do not cause steric clash for (a) neurelaxin-A, (b) compound 6, (c) compound 3 or (d) compound 2. The binding pocket is represented as a surface. (e) Polar contacts between neurelaxin-A and the binding pocket stabilize the interaction of the inhibitor with myosin II. Contacts are illustrated as black dashed lines, the protein backbone of the myosin binding pocket is shown as cartoon, the interacting residues are shown as sticks. (f) The phenyl group of neurelaxin derivatives may rotate freely, and depending on the substituting groups, it can stabilize in different conformations. Two of the several different rotamers are shown as white and black sticks in the binding pocket. (g) Polar contacts identical to those of neurelaxin-A stabilize compound 2 pyrrolo-quinone ring. Contacts are illustrated as black dashed lines, the protein backbone of the myosin binding pocket is shown as cartoon, the interacting residues are shown as sticks. (h) Additional polar contacts stabilize the binding of the phenyl ring in compound 2 compared to Neurelaxin-A. Contacts are illustrated as black dashed lines, the protein backbone of the myosin binding pocket is shown as cartoon, the interacting residues are shown as sticks.

EXAMPLES

Figure 1A:
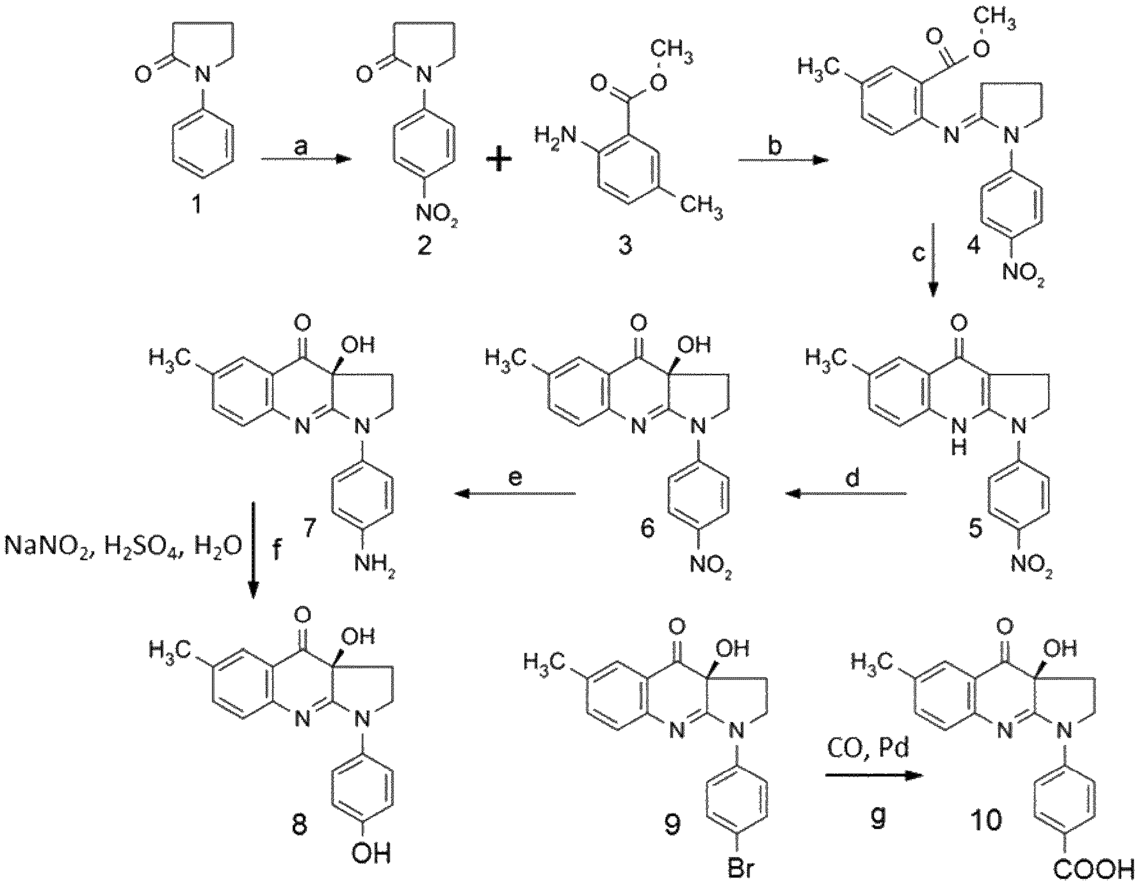
FIG. 1 is A) a scheme for the synthesis of neurelaxin-A, and compounds 5 and 3 in Table 1 and B) the NMR characterization of neurelaxin-A.

The present invention is further illustrated by the following examples.

Abbreviations

ATP: adenosine triphosphate;

$CH_3OH$: methanol;

CO: carbon monoxide;

$CO_2$: carbon dioxide;

DdMD: *Dictyostelium discoideum* myosin 2 motor domain;

DMEM: Dulbecco's Modified Eagle Medium;

DMSO: dimethylsulfoxide;

dpf: days post-fertilization;

DTT: dithiothreitol;

EDTA: ethylene diamine tetraacetic acid;

EGTA: ethylene glycol tetraacetic acid;

FCS: Foetal calf serum;

G418: Geneticin® reagent;

$H_2SO_4$: sulfuric acid;

HEPES: 4-(2-hydroxyethyl)-1-piperazineethanesulfonic acid;

MEM: minimum Essential Medium, developed by Harry Eagle;

NADH: nicotinamide Adenine Dinucleotide;

$NaNO_2$: sodium nitrite;

$NH_4HCO_2$: ammonium formate;

nm: nanometer;

NMII: non-muscle myosin 2;

$MgCl_2$: magnesium chloride;

mM: millimole per liter;

PBS: phosphate buffer saline;

Pd: palladium;

μM: micromole per liter;

RT: room temperature;

SkS1: rabbit skeletal S1 fragment.

Materials and Methods

Conditions of Spectral Measurements

Fluorescence emission spectra (λexc=350 nm) were recorded in assay buffer containing 0.1% DMSO applying the inhibitors at 5 μM concentrations. The photoconversion measurements were carried out using 5 μM neurelaxin-A in assay buffer and irradiating the samples at 480±10 nm for 0, 5, 10 and 15 minutes using a Fluorescence Spectrometer (F900, Edinburgh Instruments) equipped with a 450 W Xenon Lamp. Their absorbance spectra were measured at each time point.

Steady State ATPase Measurements

MgATPase activities of 500 nM (for basal ATPase) or 50 nM (for actin activated ATPase) SkS1 (rabbit skeletal S1 fragment) 23 and 1 μM (for basal ATPase) or 300 nM (for actin activated ATPase) DdMD were measured at increasing concentrations of neurelaxin-A in the absence or in the presence of 45 μM actin for SkS1 or 15 μM actin for DdMD. Measurements were carried out using a pyruvate kinase/lactate dehydrogenase coupled assay (NADH-coupled assay) (Kovacs M. et al., *J. Biol. Chem.* 2004, 279 (34), pp 35557-35563) at 25° C. or 20° C. in case of SkS1 or DdMD, respectively. Myosin and actin together with the indicated concentration of the inhibitor were pre-incubated for 5 minutes at room temperature and the measurements were initiated with 1 mM ATP. Data were corrected for background ATPase activity of actin. G-actin was prepared accordingly from rabbit skeletal muscle (Spudich, J. A. & Watt, S.; *The Journal of Biological Chemistry* 246, 1971, pp 4866-4871) and polymerized by 2 mM $MgCl_2$ for 1 hour at room temperature. Measurements were performed in low salt buffer containing 5 mM HEPES, 2 mM $MgCl_2$, 0.1 mM EGTA and 2 mM DTT at pH 7.2 or assay buffer containing 20 mM HEPES, 40 mM NaCl, 4 mM $MgCl_2$ at pH 7.3 for basal ATPase activity measurements with DdMD.

Cell Culture Maintenance

HeLa Kyoto H2B-mCherry eGFP-α-tubulin cells were purchased from Cell Lines Service GmbH and maintained in DMEM high glucose (4.5 g/L) supplemented with 10% FBS, 2 mM L-glutamine, 100 U/ml streptomycin, 100 μg/ml penicillin, 0.5 mg/ml G418 and 0.5 μg/ml puromycin. HeLa cells were a kind gift from Sara Tóth (Semmelweis University, Faculty of Medicine, Department of Genetics, Cell- and Immunobiology) and were maintained in low glucose DMEM (1 g/l) supplemented with 10% FBS, 2 mM L-glutamine, 100 U/ml streptomycin and 100 μg/ml penicillin. M2 cells—a kind gift of Tom Stossel and Fumihiko Nakamura (Brigham & Women's Hospital, Harvard Medical School, Translational Medicine Division)—were grown in MEM (Lonza) supplemented with 8% newborn calf serum (Sigma) and 2% FCS. The cell cultures were maintained in a humidified atmosphere of 5% $CO_2$ at 37° C. Cells were grown as monolayers in T-75 $cm^2$ culture flasks and subcultured by 0.02% EDTA (200 mg/l) 2-3 times each week when reached 90% confluency.

Conditions of Cellular Assays

For blebbing index determination, M2 cells were incubated for 30 minutes in PBS in every case prior to the addition of inhibitors, in order to initiate extensive blebbing. Blebbing of the cells was monitored before as well as after inhibitor addition to the cells. DMSO concentration was 0.1 vol/vol % in all experiments. Blebbing index was calculated by summing the initiated blebs in a 5-minute interval (starting at the indicated time points) on a given standard area 17 (whole cells with similar size, diameter=12±1 μm) and normalizing it to the blebbing index prior to inhibitor treatment.

For wound healing assays, 200 μl of HeLa cells were plated on 35 mm borosilicate glass imaging dishes at 300,000 cells/ml concentrations and incubated for 24 hours. Prior to wounding, cells were incubated in 20 μM of neurelaxin-A for an hour. After one hour, scratches were made with pipette tips in monolayer cultures and the motility of cells for occupying the wound was monitored for 24 hours with a Foculus Digital Camera (IEEE1394). Analysis of cell motility was carried out by ImageJ, by measuring the distance between two lines fitted on the two sides of the approaching cell edges created by the pipette tips.

For cell growth assays, HeLa Kyoto H2B-mCherry eGFP-α-tubulin cells were grown on an eight-chambered Lab-Tek borosilicate cover glass system, with the initial cell concentration of 100,000 cells/ml. As soon as the cells attached to the surface, they were treated with 0, 2, 5, 10, 25 or 50 μM concentrations of neurelaxin-A. Cells were grown for three days in the presence of the indicated inhibitor concentrations and cell numbers were quantified each day. The final vol/vol % of DMSO in all experiments was 0.1. Data analysis was carried out by Fiji software. On the third day of the experiment, multinuclear cells were visualized by using a Zeiss LSM 710 with a Plan Apo 20×/0.8 objective.

For Assays with Zebrafish Embryos

For the fast escape response experiments, 6 dpf larvae were placed in 50 μl drops on a plastic plate. They were treated with 0, 2, 5, 10 or 20 μM of neurelaxin-A. To evoke C-start response, acoustic stimuli were applied according to the following protocol: 10 taps were carried out with 1 minute intervals every hour for 4 hours. The force of tapping was standardized. Images were recorded with Ximea Camera (MQ003MG-CM) at 500 fps for 2 s. Data were analyzed by Flote software version 2.1 and maximal angular velocity parameters of C-start reflex were quantified. For the experiments investigating the effect of the inhibitor on the heart muscle of zebrafish, 6 dpf larvae were embedded in 1% agarose and kept in E3 in the presence of 20 μM neurelaxin-A. Videos were taken by a camera at 15.1 fps before and after inhibitor treatment every hour for 3 hours.

Fish Husbandry and Embryo Treatments

Transgenic Tg(−8.0cldnb:lynEGFP)$^{zf106}$ (cldnb:gfp) (Haas, P. & Gilmour, D., *Developmental Cell* 10, 2006, pp 673-680) zebrafish (Danio rerio) were maintained in the animal facility of Eötvös Loránd University. For the experiments investigating the skeletal and heart muscle of zebrafish, 6 dpf embryos were used. For cytotoxicity assays, 2 dpf embryos were dechorionated and placed in E3 medium (5 mM NaCl, 0.33 mM $MgCl_2$, 0.33 mM $CaCl_2$ and 0.17 mM KCl) complemented with the inhibitor in the indicated concentrations.578 PCT Cellular Toxicity Tests For phototoxicity experiments, confocal time-lapse imaging of HeLa Kyoto H2B-mCherry eGFP-α-tubulin cells for 12 hours was performed in DMEM further supplemented with 25 mM HEPES in order to achieve $CO_2$ independent media. Confocal time-lapse imaging was performed on a Zeiss LSM 710 using a Plan Apo 20×/0.8 objective, with the following parameters: 2% laser intensity at λexc=488 nm, 3% laser intensity at λexc=543 nm, 1.2× zoom, average 4, line step 1, 1000×1000 pixels, 0.35 μm pixel size, 0.65 μs dwell time, 3 slice/z-stack with 7 μm between slices at every 10 minutes.

Molecular Dynamics Simulations

Molecular dynamics simulations were carried out using GROMACS. Crystal structure of Myosin-2 Motor Domain (PDB ID 3MJX) was downloaded from the pdb database. Missing atoms of the protein were filled using Swiss-Pdb Viewer and the molecule was protonated using GROMACS's pdb2gmx module assuming pH.7. Amber99SB-ILDN force field was used, the molecule was solvated with TIP3P water molecules in a dodecahedral box with 1 nm distance between the solute and the box. Counterions (Na+) were added to neutralize the system. Force field parameters for the neurelaxin derivatives were calculated on the R.E.D. server. Neurelaxin derivatives were positioned deep in the actin binding cleft (P. Llinas et al, Developmental Cell Volume 33, Issue 4, 26 May 2015, Pages 401-412), close to the nucleotide binding pocket. Two-step energy minimization was performed, a steepest descent optimization with convergence threshold set to 500 kJ mol-1 nm-1 was followed by a conjugate gradient optimization with convergence threshold set to 10 kJ mol-1 nm-1.

The system was heated in three steps to 100 K, 200 K and then 300 K applying Berendsen barostat and thermostat. The system was equilibrated at 300 K for 1.5 ns under NPT conditions with a time step of 1 fs applying velocity rescaling thermostat. Pressure was coupled with the Parrinello-Rahman barostat with a coupling time constant of 0.5 ps, compressibility of 4.5*10-5 bar-1 and reference pressure of 1 bar. Particle Mesh-Ewald summation was used for long range electrostatics. Van der Waals and Coulomb interactions were cut off at 11 Å. For analysis, structures at every 50 ps were collected.

A. Synthesis of Neurelaxin-A

Example 1: Synthesis and Characterization of Neurelaxin-A 1.1. Synthesis

Neurelaxin-A was synthesized according to the scheme given FIG. 1*a*.

The steps a-d were led according to the experimental protocol described in Képiró et al., "para-nitroblebbistatin, the non-cytotoxic and photostable myosin 2 inhibitor", *Angew. Chem. Int. Ed.,* 2014, 53, 1-6.

The conditions for step e are given hereinafter:

Step e:

3.6 mg para-nitroblebbistatin was dissolved in 0.7 ml methanol and it was mixed with 0.7 ml cc. ammonium formate in methanol solution. A few granules of palladium black were added and the mixture was stirred for 18 hours at room temperature. A Strata XL 2 g SPA column (Phenomenex) was equilibrated with 50 ml acetonitrile then 50 ml water and the crude reaction mixture was pipetted onto the column. It was sequentially washed with 20 ml water then eluted with 20 ml acetonitrile containing 1% trifluoroacetic acid and dried in vacuum. The brownish oil was dissolved in 0.5 ml acetonitrile containing 0.1% triethylamine (TEA). The product was isolated by HPLC (Agilent 1100 instrument) using Luna 250×10 mm C18(2) column (Phenomenex). The HPLC conditions were as follows: isocratic elution, content of buffer: water (0.1% TEA): acetonitrile (0.1% TEA)=3:7, flow rate: 3.5 ml/min, detection wavelength: 254 nm. Ms (ESI): m/z=308.1 [M+H]+. Chemical purity: consistent with >95% purity (LC, 210 nm). Appearance: orange solid.

From Table 1, compound 5 and compound 3 are synthesized according to step f and step g, respectively.

Figure 1B:
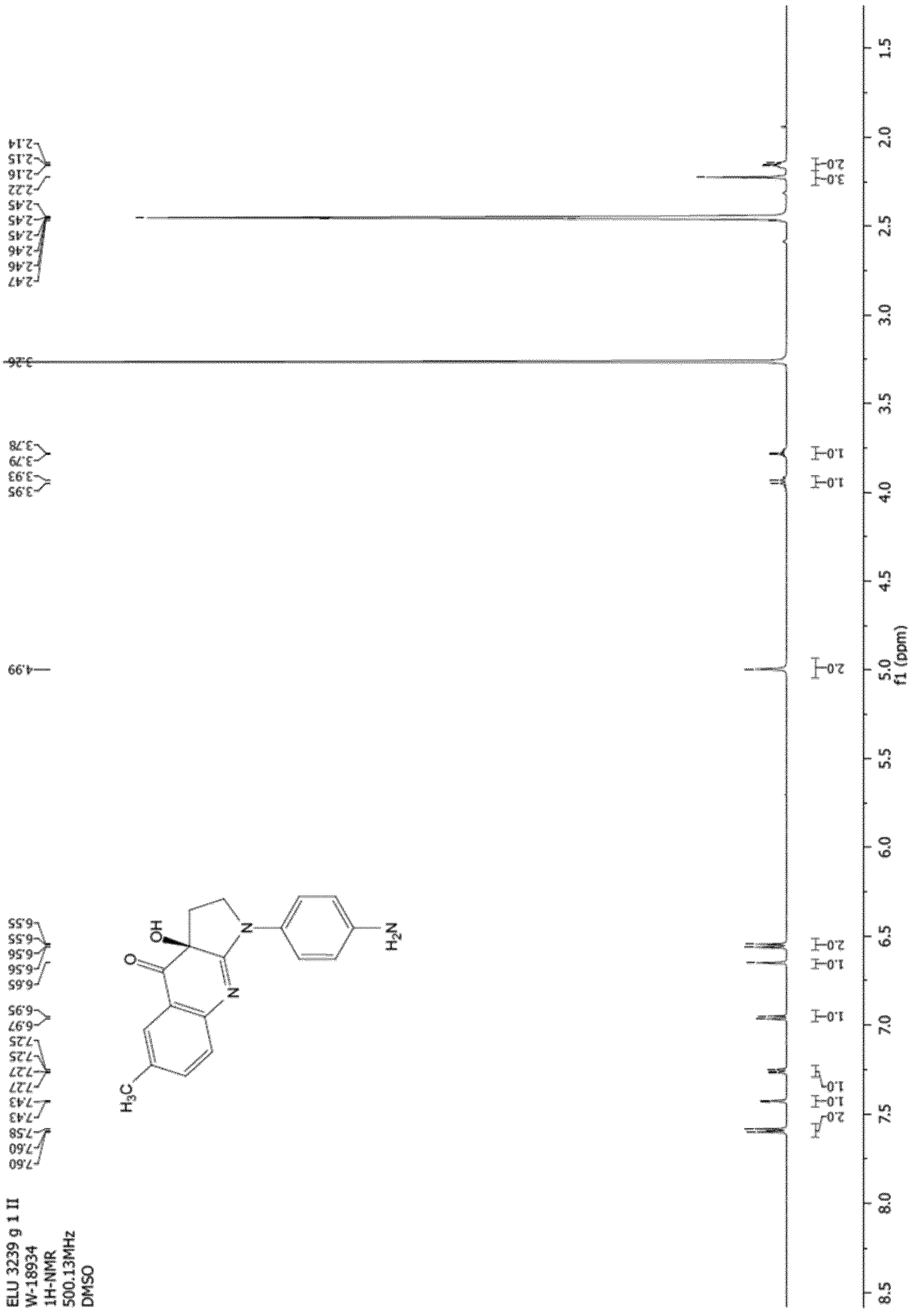

The identity of the synthetized neurelaxin-A compound was confirmed by NMR (FIG. 1*b*).

1.2. Characterization

Water Solubility

The solubility and the solution stability of neurelaxin-A, were measured in 0.1 and 1 vol/vol % DMSO at room temperature.

500 μM inhibitor solutions were prepared in assay buffer (40 mM NaCl, 4 mM MgCl2, 20 mM HEPES pH 7.3) containing 0.1 or 1 vol/vol % DMSO.

Figure 2A:
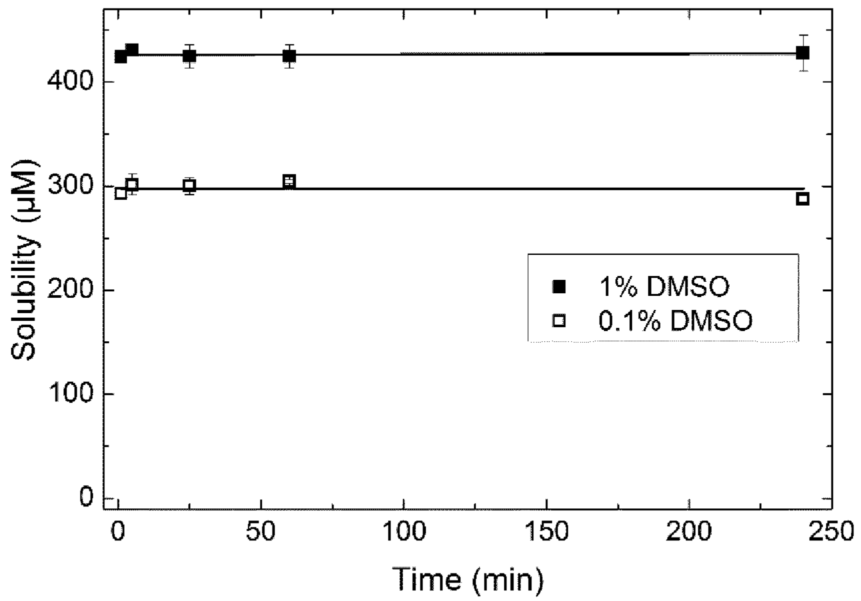
FIG. 2 is a set of graphs showing (A) the water-solubility, (B) the fluorescence and (C) the photostability for neurelaxin-A. (a) Solubility of neurelaxin-A in 0.1 or 1 vol/vol % DMSO in assay buffer. After dissolving 500 μM of Neurelaxin-A in assay buffer, the centrifugation of the precipitates yielded soluble supernatant concentrations at around 298±2.5 μM and 426±1.7 μM for 0.1 or 1 vol/vol % DMSO, respectively, and remained constant for 4 hours (data were fit to a linear function). (b) Fluorescence spectrum of 5 μM neurelaxin-A at λexc=350 nm compared to 5 μM blebbistatin, another myosin 2 inhibitor. (c) Absorbance spectrum of neurelaxin-A after irradiating 5 μM of the inhibitor at 480±10 nm for different lengths of time.

After 0, 5, 25, 60 and 240 minutes, the samples were centrifuged for 1 minute. Absorption spectra of the supernatants were recorded and the concentrations of the dissolved inhibitors were determined using the extinction coefficient $\varepsilon^{o}_{427}$=6860 $M^{-1}cm^{-1}$ (FIG. 2A).

The results show that the water-solubility of neurelaxin-A is strongly higher than those of other myosin 2 specific inhibitors like blebbistatin or para-nitroblebbistatin, which have a solubility of around 20 μM (Képiró et al., *Angew. Chem. Int. Ed.,* 2014) or even lower. Especially, the saturation concentrations of neurelaxin-A in 0.1 vol/vol % DMSO and 1 vol/vol % DMSO were found to be 298±2.5 μM and 426±1.7 μM respectively. At these concentrations, the solutions were stable for several days.

These results evidence the high water-solubility of neurelaxin-A contrary to other commonly used myosin inhibitors.

Fluorescence

The aim is to characterize the fluorescence of neurelaxin-A.

Fluorescence emission spectra ($\lambda_{exc.}$=350 nm) were recorded in assay buffer containing 0.1% DMSO comprising the inhibitor at 5 μM concentration.

Figure 2B:
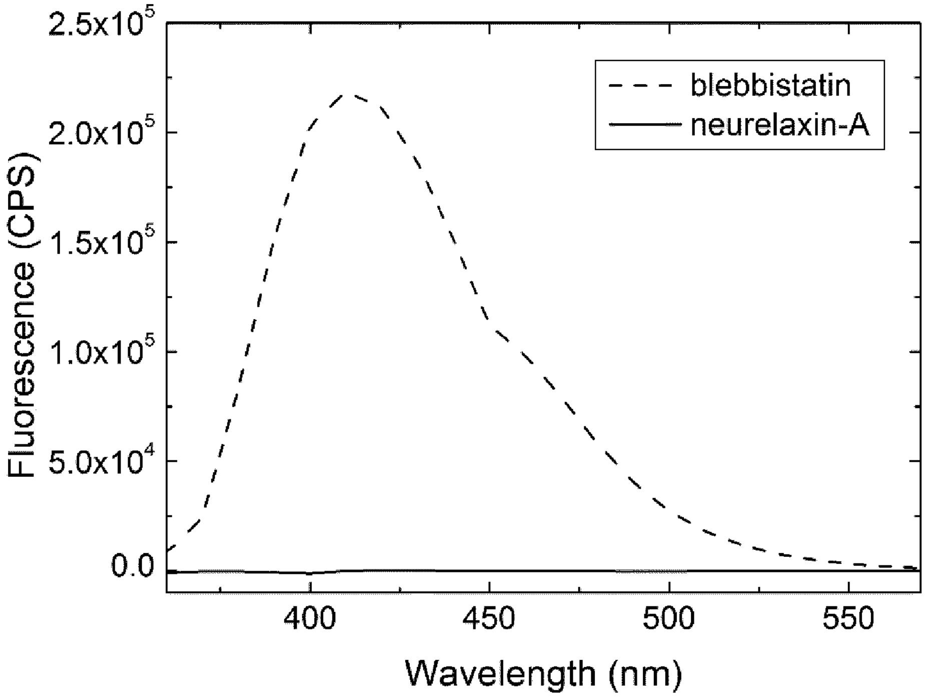

The results are presented FIG. 2B and show that there is no fluorescence signal for neurelaxin-A contrary to a similar myosin 2 specific inhibitor blebbistatin.

Without willing to be bound by any theory, the Applicant thinks that neurelaxin-A is non-fluorescent due to the electron withdrawing substitution at the C15 position.

Photostability

Figure 2C:
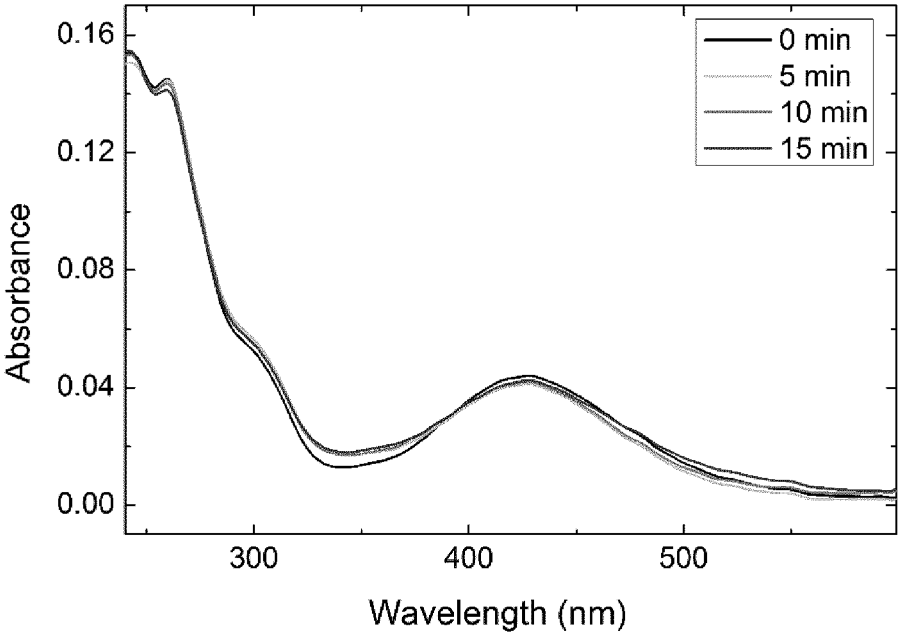

Neurelaxin-A's photostability was measured by irradiating the compound in assay buffer at 480±10 nm for 0, 5, 10 and 15 minutes and recorded the absorption spectra afterwards (FIG. 2C).

The results show that the absorption spectrum of the neurelaxin-A solution has not been altered, demonstrating photo stability.

1.3. General Conclusions

These experiments evidence that neurelaxin-A is a water soluble, non-fluorescent and photostable small molecule, which characteristics allow efficient testing of the in vitro and in vivo myosin inhibitory properties. Furthermore, these characteristics are essential for carrying out tests on animal models and functional tests on neurons.

B. Biological Tests—Toxicity and Inhibitory Properties

The aim is to prove that on one hand neurelaxin-A is not toxic or cytotoxic; and on the other hand, neurelaxin-A is an efficient myosin 2 inhibitor. In vitro and in vivo tests were led.

Example 2: Characterization of Inhibitory Properties of Neurelaxin-A

After the physico-chemical characterization of neurelaxin-A, its in vitro and in vivo inhibitory properties were characterized.

2.1. In Vitro ATPase Activity

Figure 3A:
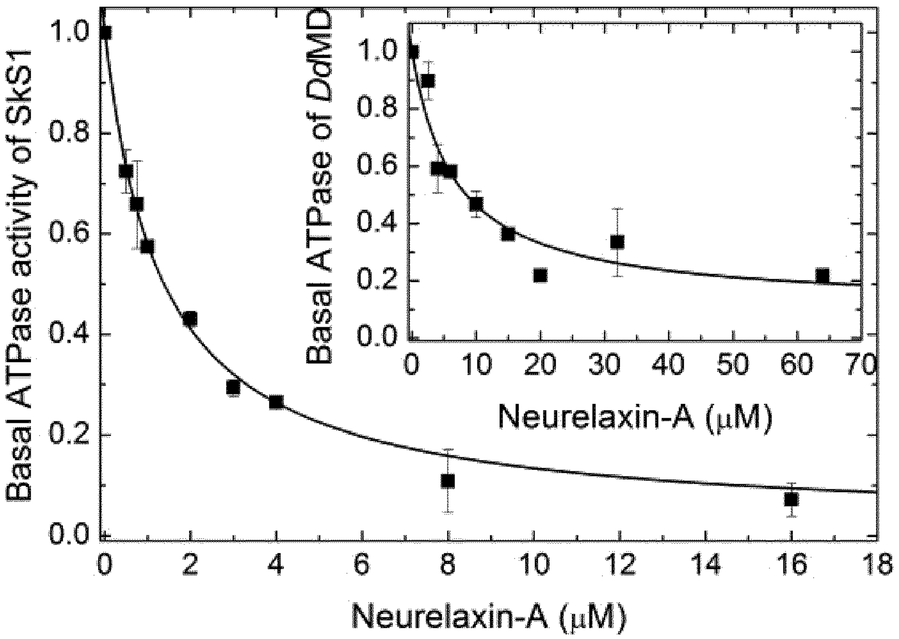
FIG. 3 is a set of graphs showing the in vitro and in vivo inhibitory properties of neurelaxin-A. (a) (b) in vitro inhibition of basal (a) and actin activated (b) ATPase activity of rabbit skeletal S1 (SkS1) and *Dictyostelium discoideum* myosin 2 motor domain (DdMD) at increasing concentrations of neurelaxin-A. Data (means±s.d. from three independent experiments) were normalized to ATPase activities at 0 μM inhibitor concentrations and were fitted with hyperbolic functions yielding basal ATPase activity inhibition with IC50=1.3±0.1 μM, for SkS1 and IC50=6.6±2 μM, IC50 for DdMD. Hyperbolic fits to actin activated ATPase activities yielded IC50=0.47±0.06 μM, for SkS1 and IC50=6.7±1.9 μM for DdMD. (c) Blebbing indices of M2 cells in the presence of increasing concentrations of neurelaxin-A. Blebbing index values are normalized to the starting point. Data were fitted with exponentials yielding rate constants of inhibition for 5, 10, 25 and 50 μM of the inhibitor. (d) Relative migration of HeLa cells measured after 24 h in the absence (Control) or in the presence of 20 μM neurelaxin-A were 30.6±5.4% for Control, 62.6±3.6% for neurelaxin-A, 100% is considered as the total diameter of the wound (n=6 scratches, from two independent experiments). (e) Representative images of wound healing assays immediately after scratching (0 min) and after 24 h incubation with 20 μM neurelaxin-A or without the inhibitor (Control). White lines mark the cell edges at 0 minutes. (f) (g) Inhibition of HeLa cells division by neurelaxin-A. The ratio of multinuclear cells (f) increases while the total cell number (g) decreases after neurelaxin-A treatment. Cell numbers after 3 days of treatment were normalized to 0 μM inhibitor concentrations counted on the first day of the experiment. Data (means±s.d., n=50-100) were fitted with hyperboles yielding IC50=17.8±4.7 μM values for the half-maximal inhibition of cell number growth of HeLa cells. (h) Relative rate of muscle contraction calculated as the ratio of the maximal angular velocity of the head during C-start escape of zebrafish in the absence (Control) and presence of 2 μM Neurelaxin-A. Medians (n=30) of the parameter maximal angular velocity of C-start are presented in the function of time. Half-inhibition occurs is at 3.2 hours. (i) Heart rate (left panel) and amplitude of heartbeat (right panel) of zebrafish embryos before and after 3 hours of 20 μM neurelaxin-A treatment.
Figure 3B:
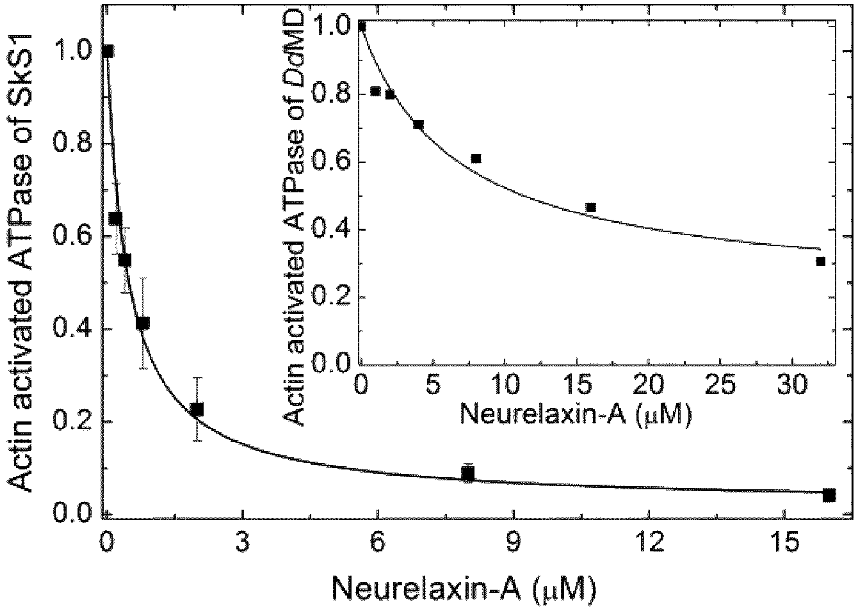

The basal and actin activated ATPase activities of rabbit skeletal muscle myosin S1 (SkS1) and *Dictyostelium discoideum* myosin 2 motor domain (DdMD) were measured at increasing concentrations of neurelaxin-A (FIGS. 3A and 3B).

Neurelaxin-A decreased the basal as well as actin activated ATPase activity of SkS1 to a maximal extent (~98-100%) yielding half-maximal inhibitory concentration values of IC50=1.3±0.1 μM for the basal ATPase of SkS1 and IC50=0.47±0.06 μM for the actin activated ATPase activity of SkS1. Neurelaxin-A reached 90% and 80% inhibition on basal and actin activated ATPase activities of DdMD yielding half-maximal inhibitory concentration values of IC50=6.6±2 μM for the basal ATPase and IC50=6.7±1.9 μM for the actin activated ATPase activity of DdMD.

In conclusion, based on the steady state ATPase measurements, neurelaxin-A is specific inhibitor of skeletal muscle myosin and Dictyostelium myosin 2 in vitro.

2.2. Inhibition in Human Melanoma (M2) and HeLa Cells

Then, characterization of the non-muscle myosin 2 inhibition by neurelaxin-A was led in cellular assays, namely in human melanoma (M2) and HeLa cell cultures.

2.2.1. Inhibition of Blebbing in M2 Cell Culture

Figure 3C:
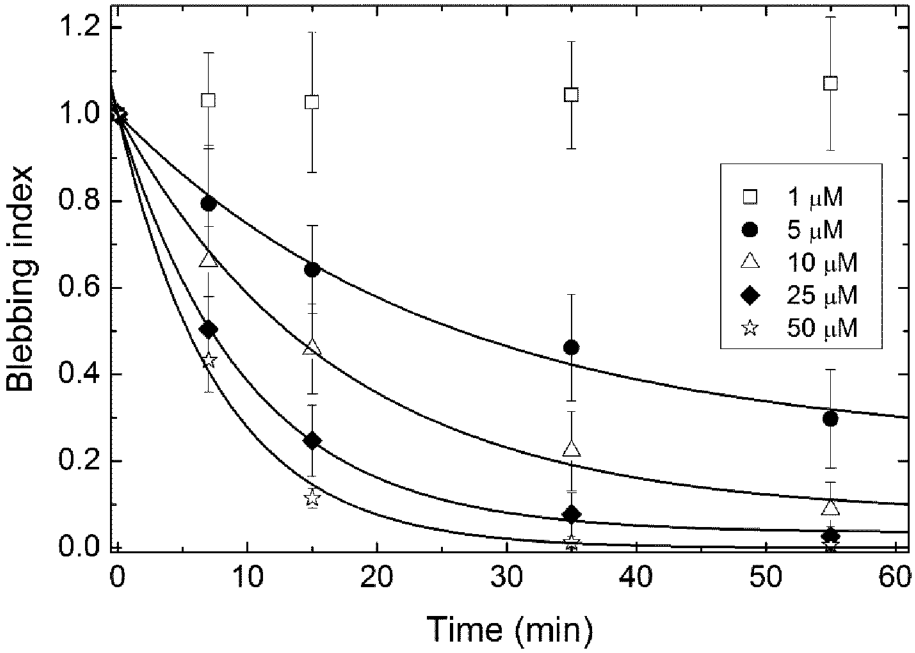

As myosin 2 inhibition blocks blebbing of M2 cells (Straight et al., *Science,* 2003, 299 (5613), pp 1743-7), the blebbing indices ((Charras, G. T., Yarrow, J. C., Horton, M. A., Mahadevan, L. & Mitchison, T. J. Non-equilibration of hydrostatic pressure in blebbing cells. Nature 435, 365-369, doi:10.1038/nature03550 (2005))) of M2 cells were measured in time, after incubating the cells in neurelaxin-A at different concentrations (FIG. 3C).

The results show that even 5 μM concentrations of the myosin 2 inhibitors achieved significant decrease in the blebbing indices of the cells within an hour, whereas higher concentrations of the inhibitors completely stopped blebbing of the cells within >40-60 minutes (10 μM) or >20 minutes (25 and 50 μM).

The time constants for the inhibitor uptake of M2 cells based on the suppression of blebbing index are summarized in Table 3.

TABLE 3

Inhibition of blebbing of M2 cells.

| Concentration | 5 μM τ (min) | 10 μM τ (min) | 25 μM τ (min) | 50 μM τ (min) |
|---|---|---|---|---|
| Neurelaxin-A | 25.0 ± 4.3 | 16.8 ± 1.6 | 9.9 ± 0.3 | 7.8 ± 0.3 |

2.2.2. Motility Tests in HeLa Wound Healing Assay

Myosin 2 inhibition inhibits or enhances motility of different cell lines on different substrates and on 2D or 3D environments (Sarkar, S.; Egelhoff, T.; Baskaran, H., "Insights into the Roles of Non-Muscle Myosin 2a in Human Keratinocyte Migration." *Cellular and molecular bioengineering* 2, 486-494, doi:10.1007/s12195-009-0094-2 (2009)), and seems to moderately enhance the motility of HeLa cells on 2D surfaces (~140% compared to 100% of the control) (Nakayama, M. et al., Rho-kinase and myosin 2 activities are required for cell type and environment specific migration. Genes to cells: devoted to molecular & cellular mechanisms 10, 107-117, doi:10.1111/j.1365-2443.2005.00823.x (2005)).

To test the effect of neurelaxin-A on the motility of HeLa cells on uncoated glass surface, wound-healing assays were carried out in the absence and in the presence of 20 μM concentrations of the inhibitor.

After 24 h, the percent of migration was measured for each sample. The control corresponds to a sample in the absence of inhibitor.

The results (FIGS. 3D and 3E) show that the inhibitor increased motility of HeLa cells compared to untreated cells, quantified after 24 hours of incubation (30.6±5.4% for control, 62.6±3.6% for neurelaxin-A, where 100% is considered as the total diameter of the wound).

2.2.3. Inhibition of Cytokinesis of HeLa Cell Culture

Figure 3G:
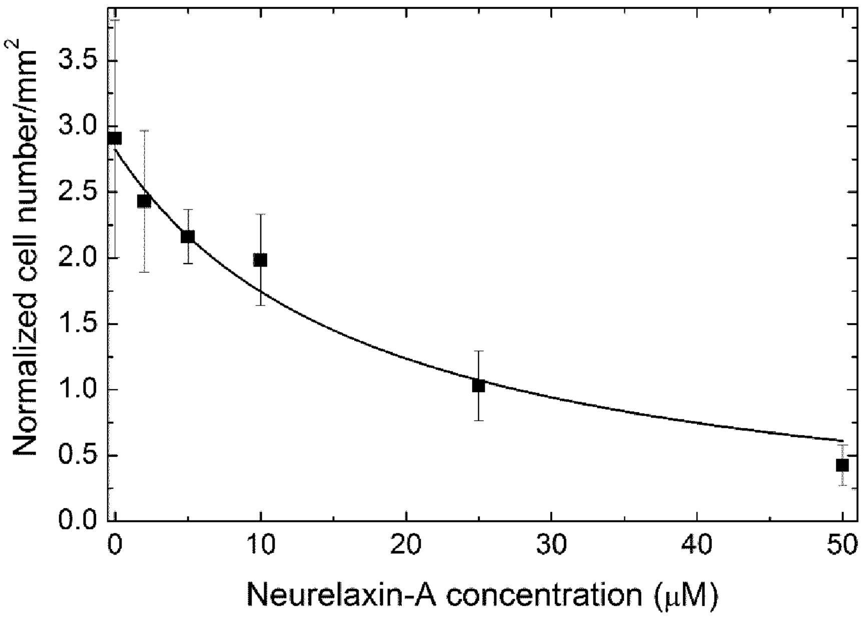

Another important phenotypic effect of non-muscle myosin 2 inhibition is the blocking of cytokinesis and consequently, the increasing number of multinucleated cells and the relatively low total cell number in human cancer cell cultures (Straight et al. Science, 2003, 299 (5613), pp 1743-1747). Therefore, the ratio of multinuclear cells and total cell number of HeLa cells was measured in time at different concentrations of neurelaxin-A (FIGS. 3F and 3G).

Figure 3H:
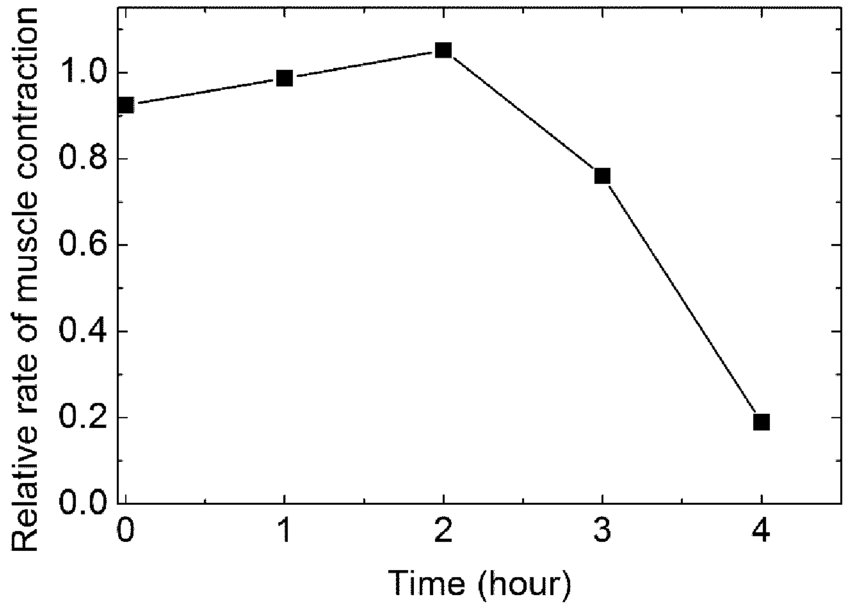

Cells incubated in different concentrations of the inhibitors were counted on each day for three days. On the 3rd day of the experiment, cell number in the absence of inhibitor (0 μM) increased to 3-3.5 times of the initial cell number, whereas 25 μM of the inhibitor completely inhibited cytokinesis resulting in no significant increase in cell number. In parallel with this phenomenon, the ratio of multinuclear cells increased with increasing inhibitor concentration. The $IC_{50}$ values of the inhibition of cytokinesis based on cell number (FIG. 3H) for neurelaxin-A were calculated as $IC_{50}$=17.8±4.7 μM.

2.3. In Vivo Functional Tests on Zebrafish Embryos 2.3.1. Inhibition of Skeletal Muscle by Neurelaxin-A Since the myosin 2 inhibitors decrease the ATPase activity of SkS1 in vitro, the effect of neurelaxin-A on zebrafish skeletal muscle in vivo was studied.

The Applicant investigated the fast escape response (C-start) reflex of 6 dpf fish evoked by standardized acoustic stimuli.

During the C-start reflex, first the head of the animal rotates about the center of mass towards the direction of future escape, then the body of the animal exhibits a curvature that resembles a letter C, mediated by quick contraction of the muscles on one side accompanied with relaxation on the other side (Fetcho, J. R., "Spinal network of the Mauthner cell. Brain", *Behavior and Evolution* 37, 298-316 (1991)).

The relative rate of in vivo skeletal muscle contraction was quantified based on the velocity of the rotating heads of the animals have been quantified (maximal angular velocity) in the absence and in the presence of neurelaxin-A (2 μM), monitored for 4 hours.

The results (FIG. 3H) show that the half maximal effective concentration (EC50) value for the inhibition of the maximal angular velocity by neurelaxin-A was found to be EC50<2 μM.

The results also evidenced that the inhibitory effect of neurelaxin-A is exerted relatively slowly due to its slower uptake (half inhibition occurred at 3.2 hours).

2.3.2 Inhibition of Cardiac Muscle by Neurelaxin-A

To further evaluate the specificity of neurelaxin-A on different myosin 2 isoforms, the effect of the inhibitors on 6 dpf zebrafish heart muscle in vivo was studied.

Heart beating and the amplitude of heart muscle contraction were monitored before and after the addition of 20 μM of neurelaxin-A to the zebrafish, imaging the same embryos every hour for three hours.

Figure 3I:
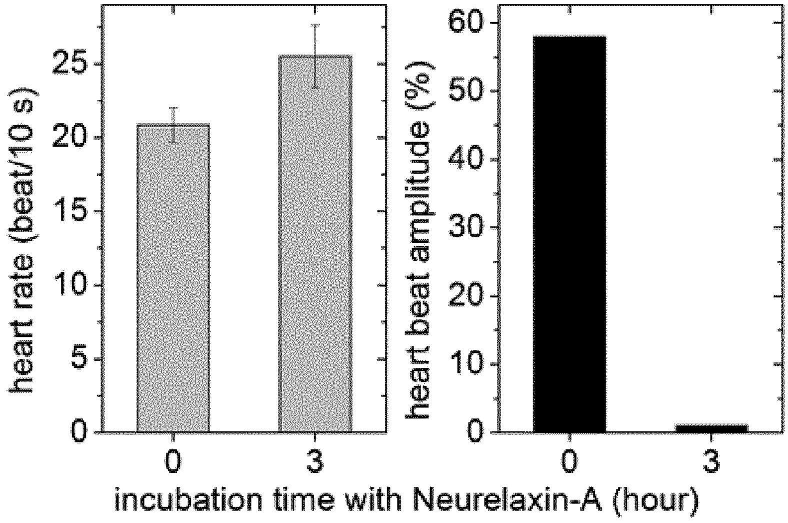

The results (FIG. 3I) show that by the addition of the inhibitors, the pulse rate (heart beats/time) did not change substantially in the first three hours (between 120 and 130 beats/minute). In contrast, the amplitude of contraction dropped drastically already within three hours.

2.4. Conclusion

In conclusion, based on the steady state ATPase measurements, neurelaxin-A is specific inhibitor of skeletal muscle myosin and Dictyostelium myosin 2 in vitro. Based on cellular and animal tests, neurelaxin-A is also an efficient inhibitor of skeletal muscle myosin, heart muscle and non-muscle myosin 2s in vivo.

Example 3: Neurelaxin-A is Non-Cytotoxic

The aim is to conduct preliminary tests on toxicity of neurelaxin-A. Cellular and in vivo zebrafish tests were conducted combined with imaging.

3.1. HeLa Cell Toxicity Tests

Figure 4A:
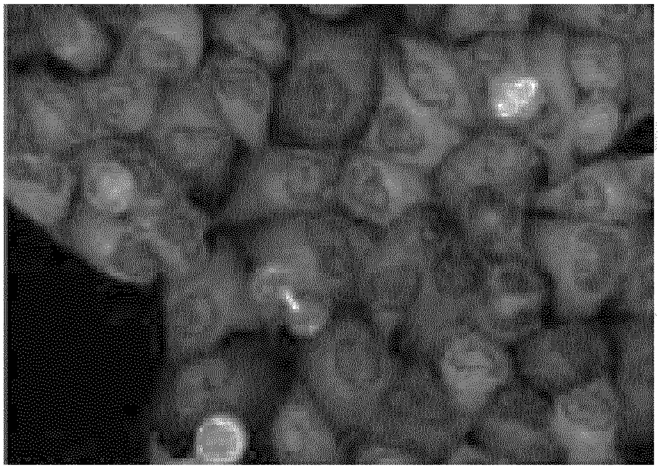
FIG. 4 is a set of a graph and images representing toxicity assays with neurelaxin-A. (a) Maximum intensity projections of fluorescent confocal microscopic z-stack images of EGFP-α-tubulin H2B-mCherry HeLa Kyoto cells at the beginning (a) and at the end (b) of a 12-hour time-lapse imaging in the presence of 50 μM neurelaxin-A. (c) For reference, the well-known cytotoxic effects of blebbistatin are shown (white arrowhead). (d) Lifespan cytotoxicity assays of zebrafish embryos (n=20) incubated at increasing concentrations of Neurelaxin-A.

To test the cytotoxicity of neurelaxin-A in live-cell fluorescence microscopy, time-lapse EGFP-α-tubulin H2B-mCherry labeled HeLa Kyoto cells were imaged in a confocal microscope (FIG. 4*a*).

Cells were treated with 50 μM neurelaxin-A and imaged for 12 hours applying 3 z-sections every 10 minutes.

Figure 4B:
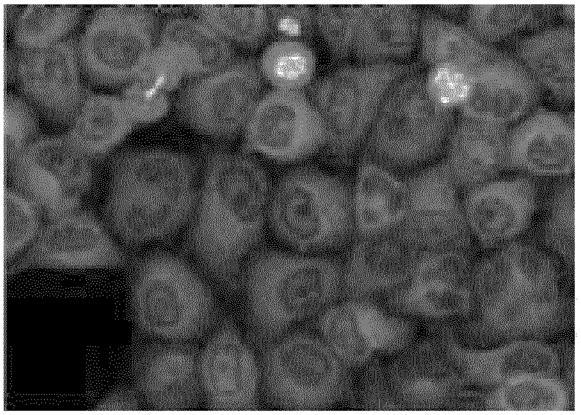

The results show that cells receiving neurelaxin-A treatment did not show any signs of toxicity after 12 hours (FIG. 4*b*).

Figure 4C:
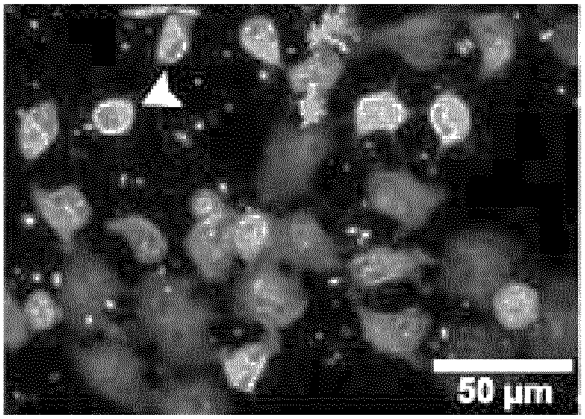

Treatment with blebbistatin was used as positive control to demonstrate phenotypic effects of cell death (FIG. 4*c*): cells round up from the surface and eventually die. This is accompanied by their increased autofluorescence and fragmented, dense nuclei. An example for such cytotoxic phenotype is marked on FIG. 4*c* with a white arrowhead. Blebbistatin's cytotoxic effects are independent of its myosin inhibition.

3.2. Zebrafish Toxicity Tests

Figure 4D:
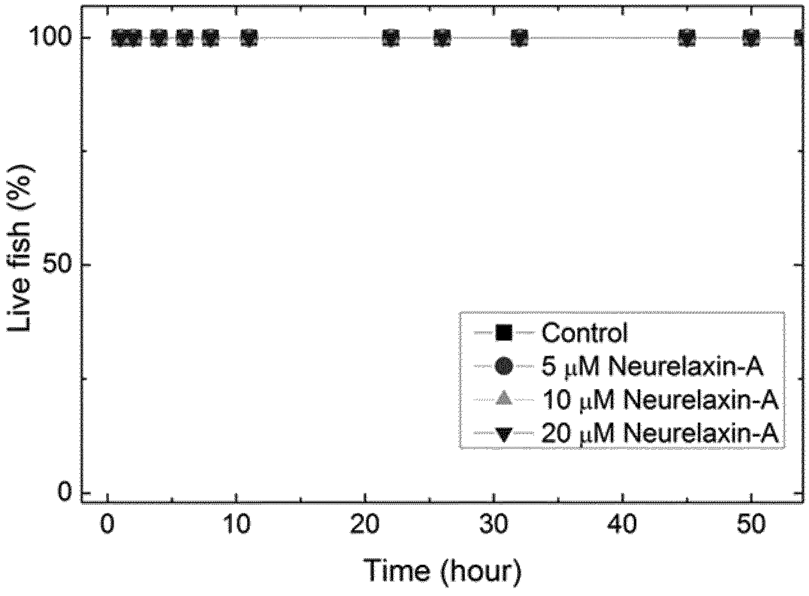

In order to test the cytoxicity of neurelaxin-A in a live animal model, zebrafish embryos were treated with the inhibitor at different concentrations and their development was followed for 72 hours (FIG. 4*d*).

The results show that after 40 hours, embryos treated with neurelaxin-A did not show any signs of cytotoxicity even at high concentrations and their fitness was comparable to the untreated control embryos.

3.3. Conclusion

In conclusion, neurelaxin-A owns important advantage as a potential candidate for drug development purposes such as its low cytotoxicity. Neurelaxin-A is an improved myosin 2 inhibitory compound compared to blebbistatin, because it is not cytotoxic as it was shown in cellular tests, and at the presented timescale (72 hours), its in vivo application in zebrafish embryos does not cause any visible damage.

C. Biological Tests—Functional Tests on Neurons

Example 4: Effects of Neurelaxin-A on Neurons 4.1. Neurite Growth Enhancement

The aim is to demonstrate that myosin 2 inhibition by neurelaxin-A induces neurite growth.

Embryonic mouse hippocampal cells were isolated from 17-day-old embryo and cultured on poly-D-lysine coated dish in neurobasal medium complemented with B27, FCS and glutamax for 20 hours.

The growth of neurites was monitored by phase contrast microscopy after the addition of 50 μM neurelaxin-A (Imaging buffer: Extracell isotonic salt solution, buffered with 5 mM HEPES).

Figure 5:
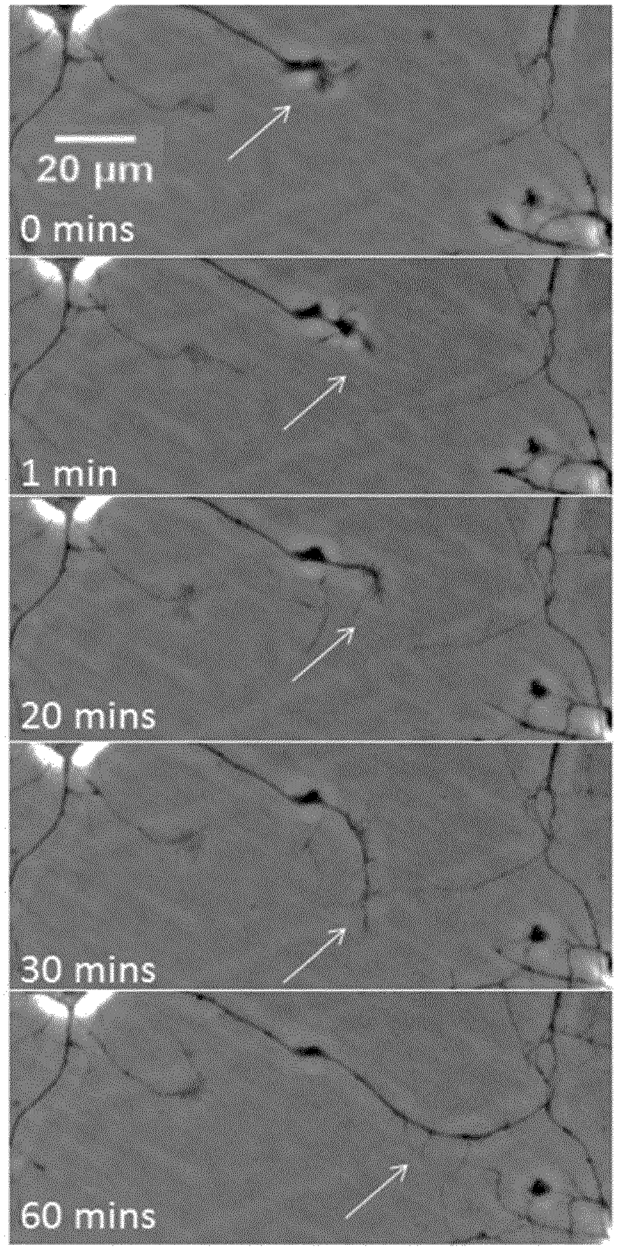
FIG. 5 is a set of images showing the induction of neurite growth by neurelaxin-A. Mouse embryonic hippocampal cell culture was treated with 50 μM neurelaxin-A at time 0. Representative images in time are shown, arrow points to the growing neurite. The addition of 50 μM Neurelaxin-A initiated a rapid (1 μm/min) growth of neurites, which resulted in the establishment of new connections.

The results (FIG. 5) show that a rapid neurite growth with a rate of approximately 1 μm/min was observed after neurelaxin-A treatment.

4.2. Axon Regeneration Enhancement

The aim is to demonstrate that myosin 2 inhibition by neurelaxin-A enhances axon regeneration.

The Mauthner neuron is a giant neuron in the hindbrain of zebrafish embryos, which is a widely used model for studying regeneration. The Mauthner axon of 3 dpf zebrafish embryos was photoablated with two-photon irradiation at 800 nm.

Figure 6:
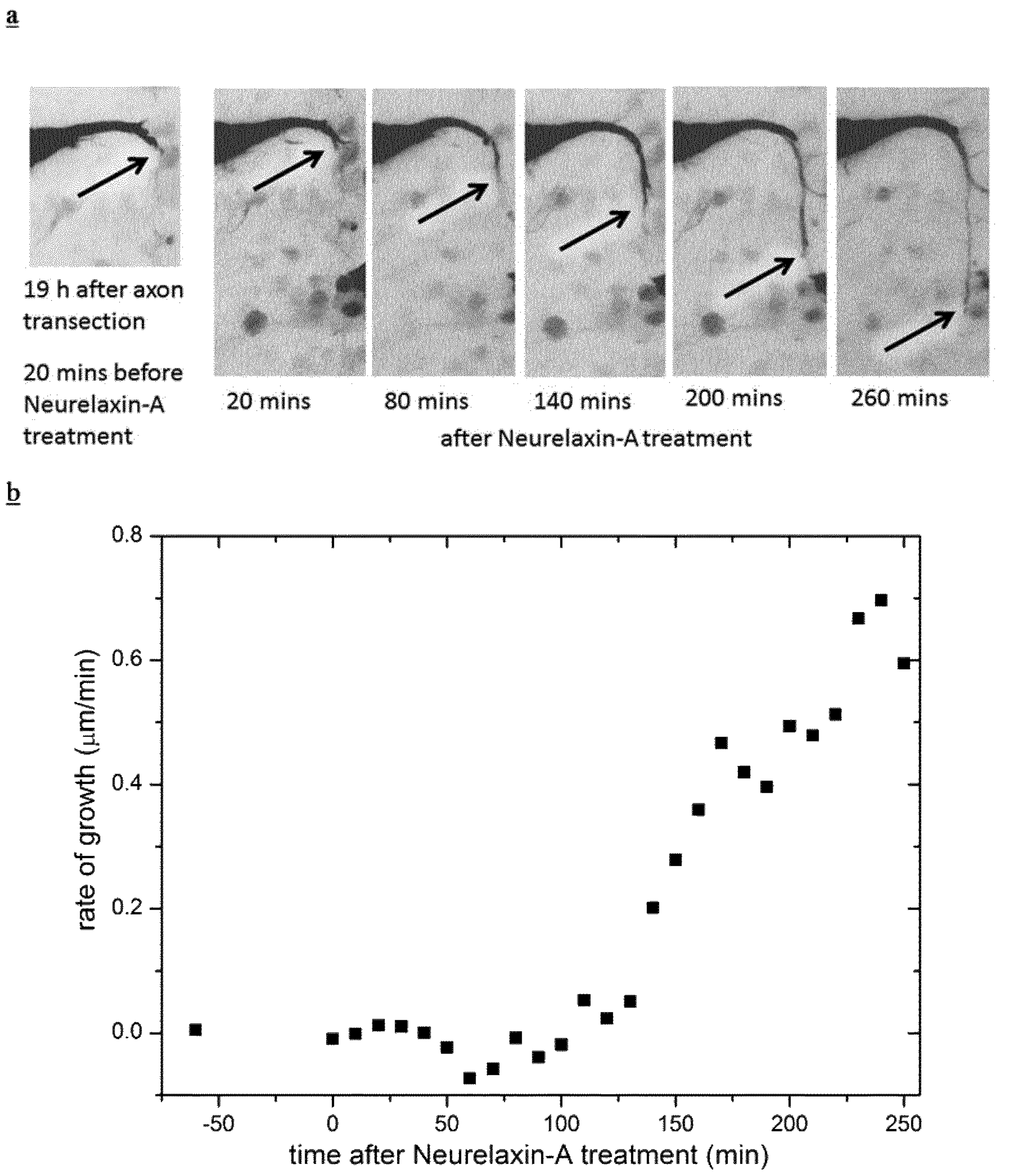
FIG. 6 is a set of a graph and images showing the induction of axon regeneration by neurelaxin-A. (a) Representative images of the regeneration of a previously laser ablated axon after treatment with Neurelaxin-A. (b) Rate of axon growth induced by neurelaxin-A.

After neurelaxin-A treatment, the spontaneous regrowth of the axon (which starts normally after 30 hours) was induced as early as 19 hours post-ablation (FIG. 6*a*). Treatment induces the regrowth of the axon after 1 hour and the maximum rate of growth is 0.6 um/min, which is reached after 2 hours of treatment (FIG. 6).

4.3. Effect of Neurelaxin-A Pretreatment on Cannabinoid-Induced Growth Cone Retraction The aim is to demonstrate that myosin 2 inhibition by neurelaxin-A prevents cannabinoid-induced structural effects in neurons.

Embryonic rat hippocampal neurons were isolated from 18-day-old embryo and cultured on poly-D-lysine coated dish in Neurobasal medium complemented with B27, FBS and glutamax for 6 days and transfected by using Lipofectamine 2000 with DNA codig for LifeAct-mCherry and CB1R-CFP.

The growth of neurites were monitored by fluorescent miscroscopy after the addition of different pre-treatment doses of neurelaxin-A at 20 minutes, followed 20 minutes later by the addition of 100 nM of the synthetic cannabinoid WIN55,212-2 as described in Roland et al, 2014.

Figure 7A:
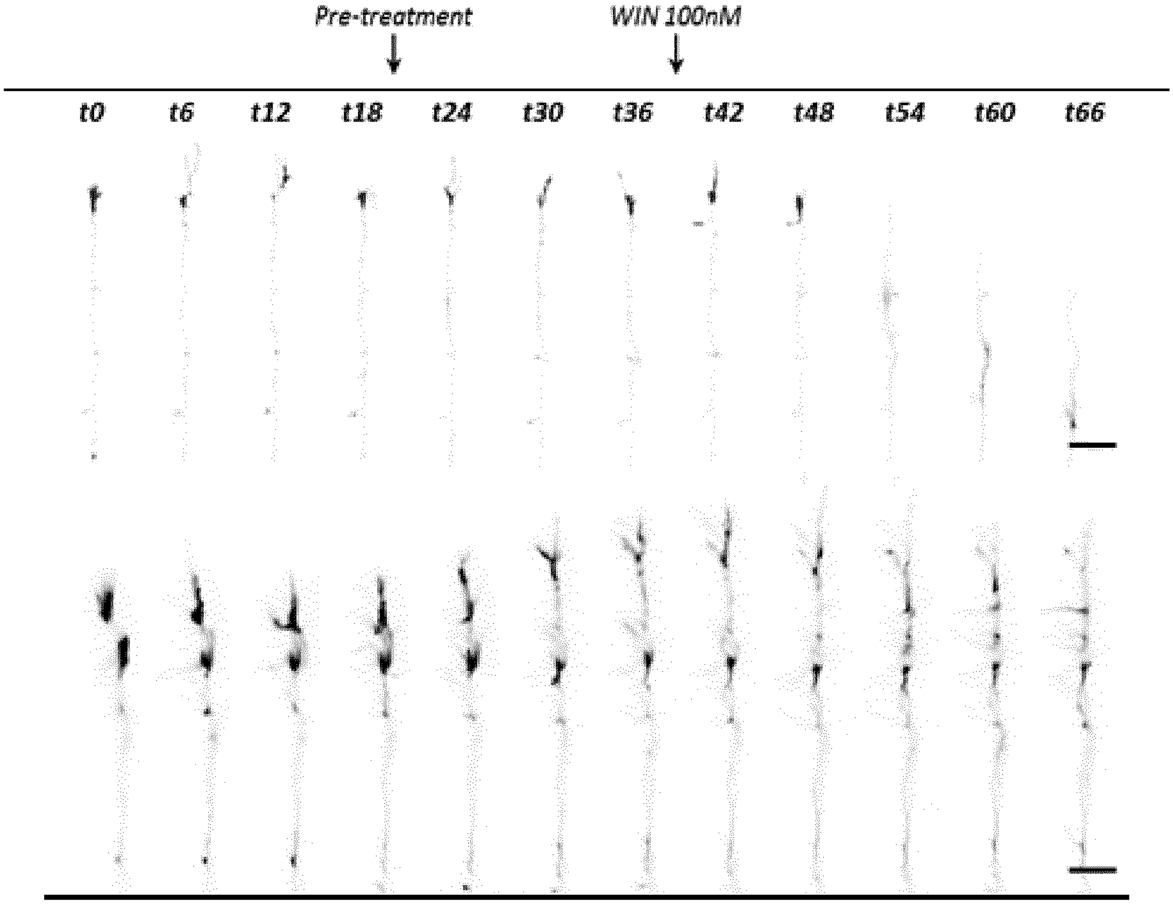
FIG. 7 is a set of representative kymographs (a) and a graph (b) of an axonal growth cone expressing LifeAct-mCherry to label F-actin pre-treated with vehicle (a, top panel) or 100 μM neurelaxin-A (a, bottom panel) at t20 min and then treated with the synthetic cannabinoid WIN55, 212-2 (WIN) 100 nM at t40 min. Scale bar=25 μm. The graph on (b) shows the quantitative effect of Neurelaxin-A (NRLX) treatment on the WIN effect (PRE=10 min before WIN exposure POST=20 min after WIN exposure, One-way ANOVA followed by a Bartnett post hoc test, ** means p<0.01 as compared to Vehicle).
Figure 7B:
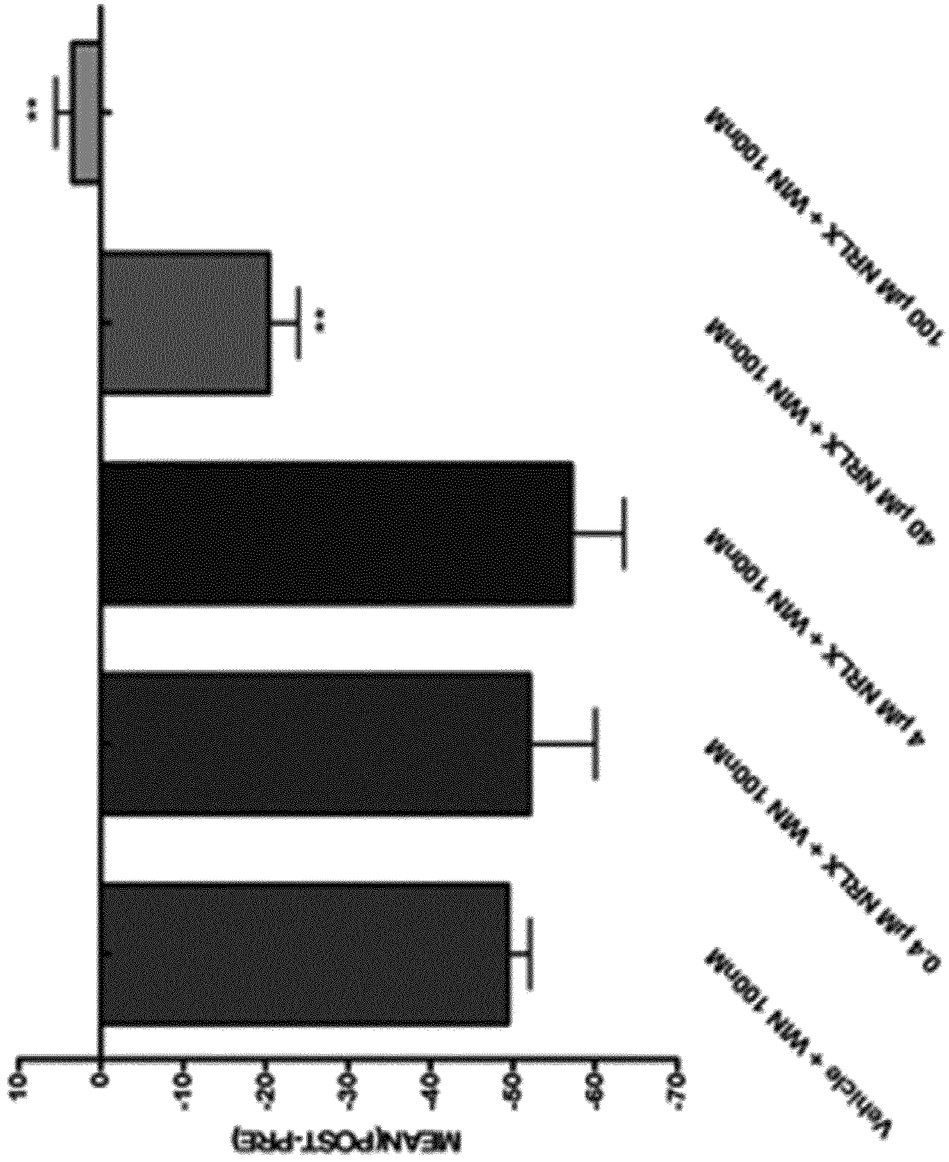

The results (FIG. 7) show that Neurelaxin-A (100 μM) significantly prevented cannabinoid-induced retraction of axonal growth cones in cultured rat hippocampal neurons following WIN55,212-2 exposure. Furthermore, as observed above, Neurelaxin-A promoted expansion and growth of terminal axons.

4.4. Effect of Neurelaxin-A Pretreatment on Oxidative Stress Resistance

In central nervous system, oxidative stress results in a secondary damage that contributes to hinder the regeneration process. It may be induced either from inflammation and macrophage activity or due to ischemia resultant from the privation of regular oxygen flow in damaged areas.

The aim is to demonstrate that Neurelaxin-A improves oxidative stress resistance occurring when central nervous system is damaged.

Protocol

Hydrogen Peroxide ($H_2O_2$) is used for generating reactive oxygen species and consequently, leading to oxidative stress and neuronal loss.

In this experiment, the neurons were first incubated with 30 μM of $H_2O_2$ or not (witness sample). Then, the neurons were treated with DMSO solutions with or without Neurelaxin-A.

Results

Figure 8:
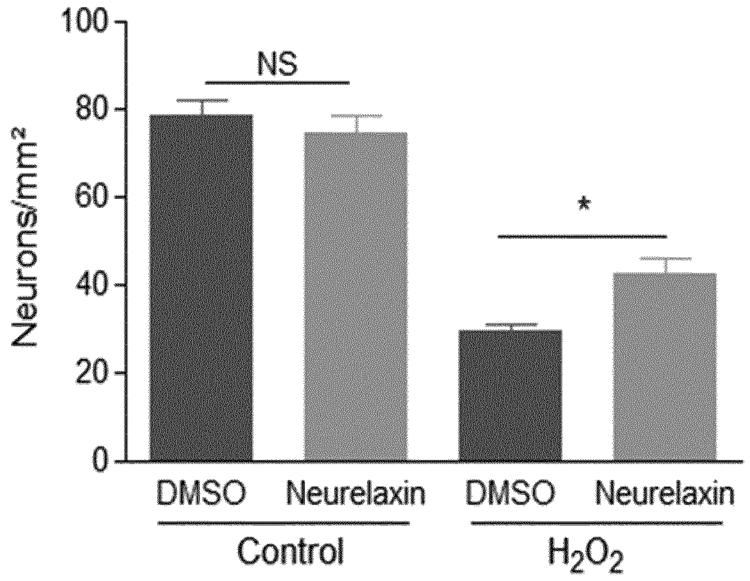
FIG. 8 is a graph showing the induction of oxidative stress resistance by neurelaxin-A. Especially, the histograms show the number of living neurons after being incubated with 30 μM of hydrogen peroxide or not (control) and then, treated with solutions of DMSO comprising or not Neurelaxin A.

The results (FIG. 8) show that when treated with Neurelaxin A, the neuronal survival and axon maintenance is increased. Thus, Neurelaxin A is an efficient compound for improving oxidative stress resistance in central nervous system.

4.5. Conclusion

The use of Neurelaxin-A enhances neurite growth, prevents cannabinoid-induced neurite retraction in cultured intact neurons and facilitates axon regeneration after axon photoablation in zebrafish embryos. These observations indicate that Neurelaxin-A is a potential promising inhibitor in the treatment of connectivity related neuropsychiatric diseases and other myosin-mediated diseases.

D. In Silico Modelling of Binding Site

Example 5: Neurelaxin Binding to Myosin

The aim is to demonstrate that neurelaxin-A derivatives have the potential to become efficient and selective myosin 2 inhibitors.

The binding of neurelaxin-A, and three other derivatives, compounds 2, 3 and 6 in Table 1 were modelled in an in silico molecular dynamics simulation series. The Applicant found that substitutes at meta and para position of the phenyl group in neurelaxin do not cause steric clash in myosin deep in the actin-binding cleft near the nucleotide binding pocket (FIG. 9*a-d*). Thus series of substitutions at these positions may form efficient myosin 2 inhibitors. Furthermore, isosteric phenyl group replacement with or without group substitutions also fit the binding pocket space in myosin, therefore they may also form efficient neurelaxin derivatives.

The polar contacts that are likely to stabilize neurelaxin-A in the binding pocket were analysed.

The stereospecific hydroxyl group of the quinoline ring and the nitrogen in the pyrrolo ring establish direct hydrogen bonds with GLY240 backbone amide and LEU262 backbone oxo groups, respectively. The oxo-group establishes hydrogen bond with the SER456 backbone oxo group through a water molecule (FIG. 9*e*).

The substituted phenyl group in neurelaxin-A does not have specific polar contacts, therefore the chemical space is potentially large which could be used for optimizing the compound for drug development. Moreover there is enough room for virtually free rotation of the substituted phenyl group (FIG. 9*f*).

By introducing a carboxyl group to the phenyl ring, the number of polar interactions between the inhibitor and the binding pocket increase substantially. The protein ligand interactions involving the hydroxyl, oxo and nitrogen groups in the pyrrolo-quinoline ring are not affected by the carboxyl group substitution: the hydroxyl group and the nitrogen establish direct hydrogen bonds with GLY240 backbone amide and LEU262 backbone oxo groups, respectively. The oxo-group establishes hydrogen bond with the SER456 backbone oxo group through a water molecule (FIG. 9*g*). Additional protein-ligand interactions are established related to the carboxyl group on the phenyl ring: salt bridge between carboxyl group and LYS265 amino group and several hydrogen bonds between the carboxyl group and the backbone of the surrounding binding pocket (FIG. 9*h*).

Conclusion

Phenyl group substitution by small hydrophilic groups does not hinder the steric fit in the binding pocket.

E. Biological Tests—Central Nervous System Regeneration

Example 6: Effects of Neurelaxin-A on Spinal Cord Injury

The aim is to demonstrate that neurelaxin A derivatives are efficient drugs for positively regenerating central nervous function.

In this experiment, a complete section of the spinal cord on animals was carried out. Then, neurelaxin A administration was carried out at the injury site, 5-10 min after the injury was performed. This neurelaxin-A administration was carried out via a diluted solution of 10 mM of neurelaxin A in a 10% DMSO/90% aCSF (artificial cerebrospinal fluid) solution, leading to an orange bright precipitate that is slowly soluble into the injury site. Finally, a BBB (Basso, Beattie and Bresnahan) analysis is performed in order to study the sequence of functional locomotor recovery patterns. The scale (0-21) represents sequential recovery stages and categorizes combinations of rat joint movement, hindlimb movements, stepping, forelimb and hind limbcoordination, trunk position and stability, paw placement and tail position.

According to this test, any drug treatment which may increase the BBB scores may be considered neuroprotective in animal models.

In this experiment, treated animals (n=3) were undistinguishable from non-treated animals (n=3). The BBB scoring scale ranges from 0 to 21.

Figure 10:
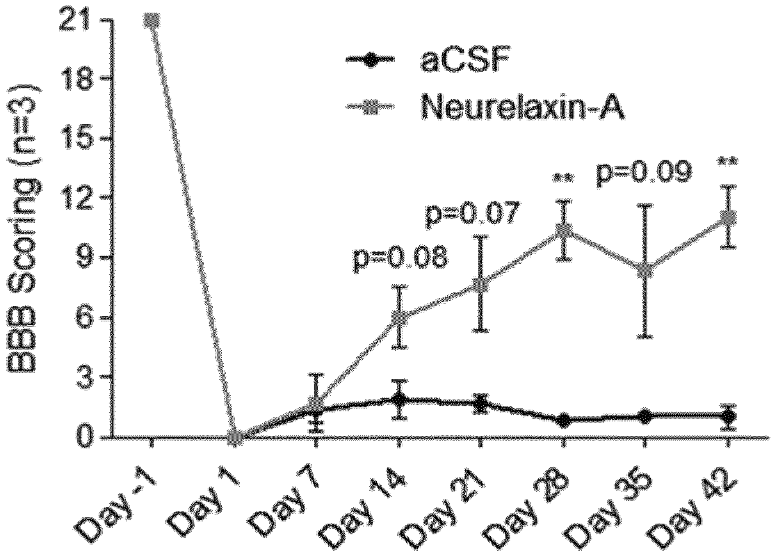
FIG. 10 is a graph showing the BBB scoring in function of time, after complete section of spinal cord in animals followed by the administration at the section site, of aCSF solution comprising Neurelaxin A or not (control) (day 1).

The results (FIG. 10) show that after complete section of spinal cord (day 1):

- without neurelaxin A treatment, the BBB scoring stays under 3 even after 42 days;
- with neurelaxin A treatment, a significant increasing of BBB scoring is registered compared to non-treated animals from day 7.

In conclusion, this test evidences that neurelaxin A is an efficient neuroprotective and neuroregenerative drug.

Example 7: Effects of Neurelaxin-A on Actomyosin in Memory and Learning

Endocannabinoid system is an important regulator of brain wiring and connectivity during development. However, the recreational intake and abuse of cannabinoids can lead to cognitive dysfunctions and memory loss.

The aim is to demonstrate that cannabinoid exposure affects particularly actomyosin activity in neurons, through activation of RhoA/ROCK pathway that causes major neuronal cytoskeleton remodeling, affecting synaptic function. Especially, the aim is to evidence that neurelaxin A and its derivatives are efficient drugs to overcome cannabinoid-induced working memory loss.

In this experiment, a novel object recognition (NOR) test was performed.

In this test animals are presented to two objects and it will explore them for a while. After, one of the objects is changed for a new and different one. Under normal circumstances animals will be attracted to the novel object and will spend more time exploring it, by comparison to the older and already known object. Animals with memory deficit will explore both objects equally.

The synthetic cannabinoid CB1R agonist CP55,940 is administrated 1 hour prior to the familiarization step. Thirty minutes prior to the familiarization animals are either treated or not with neurelaxin-A.

Figure 11:
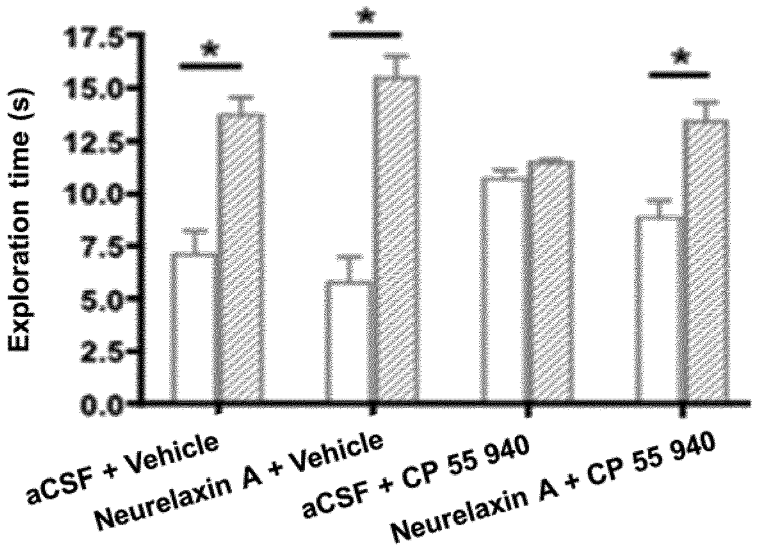
FIG. 11 is a graph showing the exploration time in the NOR test obtained by four groups of animals when the object to recognize is a familiar object (white histograms) or not (shaded histograms).

The results (FIG. 11) show that:

- animals non-treated with CP55,940 spend more time exploring the new object, independent of being treated with Neurelaxin-A or not, suggesting that Neurelaxin-A does not impact negatively the memory;
- CP55,940 treated animals spend similar time exploring both objects, demonstrating the negative effect of cannabinoid administration in memory;
- animals pre-treated with Neurelaxin-A are not affected by the cannabinoid exposure, since they will still explore more the novel object, showing no memory problems.

In conclusion, this experiment evidences that the potential of neurelaxin A to enhance synaptic function under circumstances of RhoA/ROCK pathway activation.

The invention claimed is:

1. A compound of general formula (II):

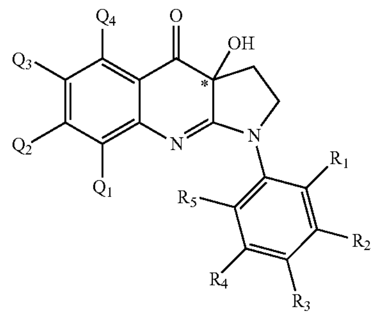

(II)

and pharmaceutically acceptable salts and/or solvates thereof, wherein:

$Q_1$, $Q_2$, $Q_3$ and $Q_4$ are each independently selected from H, halogen, alkyl, heteroalkyl, halogenoalkyl, halogenoheteroalkyl, nitro, hydroxyl, thiol and alkoxy;

$R_1$, $R_2$, $R_3$, $R_4$ and $R_5$ are each independently selected from phosphonic acid, phosphoryl, hydrogen, halogen, alkyl, heteroalkyl, halogenoalkyl, halogenoheteroalkyl, hydroxyl, nitro, thiol, alkoxy, amino, alkylamino, halogenoalkylamino, imido, alkylimido, halogenoalkylimido, hydroxylamino, alkylhydroxyamino, sulfonyl, alkylsulfonyl, halogenoalkylsulfonyl, carboxyl, carbonyl, ester, alkyloxycarbonyl, halogenoalkyloxycarbonyl, amido, alkylamido, halogenoalkylamido, formyl, alkylcarbonyl, halogenoalkylcarbonyl, formylaminocarbonyl and carboxylic acid isostere, wherein the carboxylic acid isostere is selected from the group consisting of

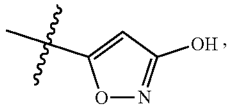

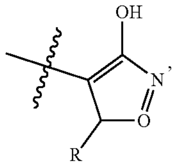

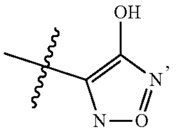

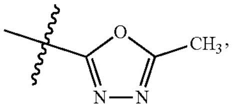

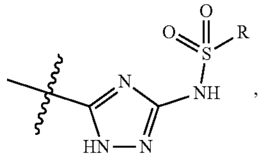

,

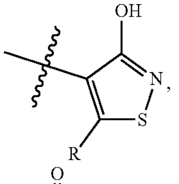

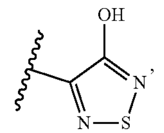

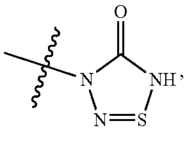

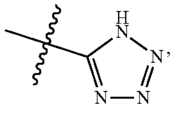

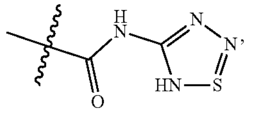

-continued

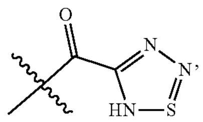

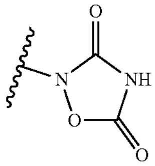

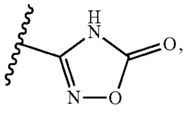

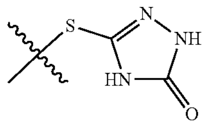

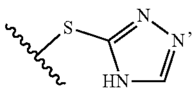

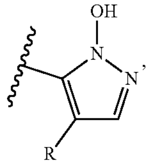

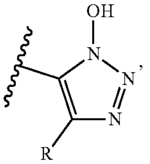

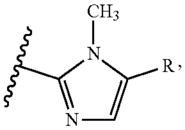

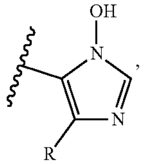

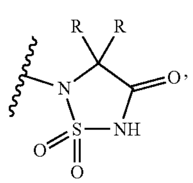

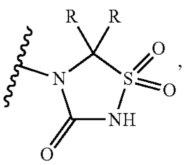

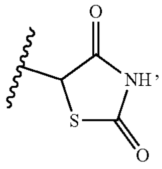

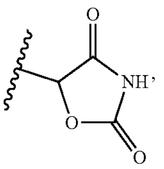

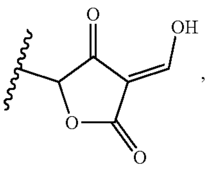

,

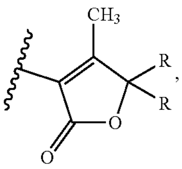

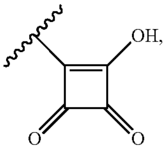

or

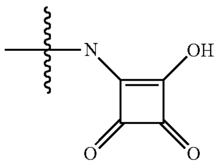

wherein R is selected from hydrogen, alkyl, halogenoalkyl, hydroxyl, thiol, alkoxy, heteroalkyl, halogenoheteroalkyl, sulfonyl, alkylsulfonyl, halogenoalkylsulfonyl, aminosulfonyl, alkylaminosulfonyl, halogenoalkylaminosulfonyl, amidosulfonyl, alkylamidosulfonyl, halogenoalkylamidosulfonyl, formyl, alkylcarbonyl, halogenoalkylcarbonyl alkyloxycarbonyl, halogenoalkyloxycarbonyl, carboxyl and phosphoryl; and

represents the point of attachment of the moiety to the rest of the molecule; and wherein at least one of $R_2$, $R_3$ and $R_4$ are a hydrophilic group selected from phosphonic acid, phosphoryl, hydroxyl, amino, carboxyl and ester having a C1-C4 alkyl chain or any charged groups thereof; and

* stands for the (R)-enantiomer, the (S)-enantiomer, the racemate or the non-racemic mixture of (R) and (S) enantiomers of the corresponding formula (II).

2. The compound according to claim 1, which is the (S)-enantiomer.

3. The compound according to claim 1, wherein $Q_3$ is methyl and $Q_1$, $Q_2$, $Q_4$, $R_1$, $R_2$, $R_4$ and $R_5$ are hydrogen; and $R_3$ is a hydrophilic group selected from phosphonic acid, phosphoryl, hydroxyl, amino, carboxyl and ester having a C1-C4 alkyl chain.

4. The compound according to claim 1, wherein the compound is selected from:

1-(4-aminophenyl)-3a-hydroxy-6-methyl-3,3a-dihydro-1H-pyrrolo[2,3-b]quinolin-4(2H)-one;

3-(3a-hydroxy-6-methyl-4-oxo-2,3,3a,4-tetrahydro-1H-pyrrolo[2,3-b]quinolin-1-yl)benzoic acid;

4-(3a-hydroxy-6-methyl-4-oxo-2,3,3a,4-tetrahydro-1H-pyrrolo[2,3-b]quinolin-1-yl)benzoic acid;

3a-hydroxy-1-(3-hydroxyphenyl)-6-methyl-3,3a-dihydro-1H-pyrrolo[2,3-b]quinolin-4(2H)-one;

3a-hydroxy-1-(4-hydroxyphenyl)-6-methyl-3,3a-dihydro-1H-pyrrolo[2,3-b]quinolin-4(2H)-one;

1-(3-aminophenyl)-3a-hydroxy-6-methyl-3,3a-dihydro-1H-pyrrolo[2,3-b]quinolin-4(2H)-one; and (4-(3a-hydroxy-6-methyl-4-oxo-2,3,3a,4-tetrahydro-1H-pyrrolo[2,3-b]quinolin-1-yl)phenyl)phosphonic acid.

5. The compound according to claim 1, wherein the compound is selected from:

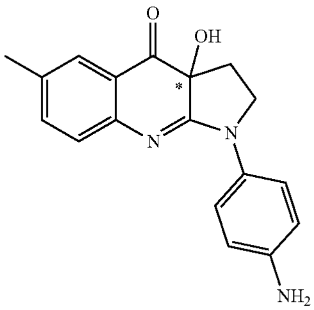

and

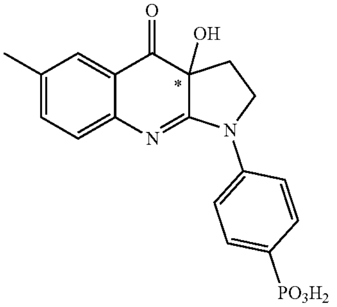

6. A pharmaceutical composition comprising at least one of a compound and pharmaceutically acceptable salts and/or solvates thereof according to claim 1, and at least one pharmaceutically acceptable carrier, diluent, excipient and/or adjuvant.

7. A medicament comprising at least one of a compound and pharmaceutically acceptable salts and/or solvates thereof according to claim 1.

8. A method of treating or preventing a myosin 2 mediated disease in a subject in need thereof, comprising administering to the subject a therapeutically effective amount of at least one of a compound of general formula (II) and pharmaceutically acceptable salts and/or solvates thereof according to claim 1.

9. The method of claim 8, wherein the myosin 2 mediated disease is a neurological, neuropathic and/or psychiatric disease or trauma.

10. The method of claim 8, wherein the myosin 2 mediated disease is selected from schizophrenia, cerebral ischemia, stroke, neuropathic pain, spinal cord injury, Alzheimer's disease, Parkinson's disease, addiction, brain cancer and multiple sclerosis.

11. The method of claim 8, wherein the compound of general formula (II) inhibits the effects of cannabinoid receptor activation.

12. The method of claim 8, wherein the compound of general formula (II) inhibits neuronal actomyosin contractility.

13. The method of claim 12, wherein the compound inhibits neuronal actomyosin contractility in vivo.

14. The pharmaceutical composition of claim 6, wherein the compound is the (S)-enantiomer.

15. The pharmaceutical composition of claim 6, wherein $Q_3$ is methyl and $Q_1$, $Q_2$, $Q_4$, $R_1$, $R_2$, $R_4$ and $R_5$ are hydrogen; and $R_3$ is a hydrophilic group selected from phosphonic acid, phosphoryl, hydroxyl, amino, carboxyl and ester having a C1-C4 alkyl chain.

16. The pharmaceutical composition of claim 6, wherein the compound is selected from:

1-(4-aminophenyl)-3a-hydroxy-6-methyl-3,3a-dihydro-1H-pyrrolo[2,3-b]quinolin-4(2H)-one;

3-(3a-hydroxy-6-methyl-4-oxo-2,3,3a,4-tetrahydro-1H-pyrrolo[2,3-b]quinolin-1-yl)benzoic acid;

4-(3a-hydroxy-6-methyl-4-oxo-2,3,3a,4-tetrahydro-1H-pyrrolo[2,3-b]quinolin-1-yl)benzoic acid;

3a-hydroxy-1-(3-hydroxyphenyl)-6-methyl-3,3a-dihydro-1H-pyrrolo[2,3-b]quinolin-4(2H)-one;

3a-hydroxy-1-(4-hydroxyphenyl)-6-methyl-3,3a-dihydro-1H-pyrrolo[2,3-b]quinolin-4(2H)-one;

1-(3-aminophenyl)-3a-hydroxy-6-methyl-3,3a-dihydro-1H-pyrrolo[2,3-b]quinolin-4(2H)-one; and (4-(3a-hydroxy-6-methyl-4-oxo-2,3,3a,4-tetrahydro-1H-pyrrolo[2,3-b]quinolin-1-yl)phenyl)phosphonic acid.

17. The medicament of claim 7, wherein the compound is the (S)-enantiomer.

18. The medicament of claim 7, wherein $Q_3$ is methyl and $Q_1$, $Q_2$, $Q_4$, $R_1$, $R_2$, $R_4$ and $R_5$ are hydrogen; and $R_3$ is a hydrophilic group selected from phosphonic acid, phosphoryl, hydroxyl, amino, carboxyl and ester having a C1-C4 alkyl chain.

19. The medicament of claim 7, wherein the compound is selected from:

1-(4-aminophenyl)-3a-hydroxy-6-methyl-3,3a-dihydro-1H-pyrrolo[2,3-b]quinolin-4(2H)-one;

3-(3a-hydroxy-6-methyl-4-oxo-2,3,3a,4-tetrahydro-1H-pyrrolo[2,3-b]quinolin-1-yl)benzoic acid;

4-(3a-hydroxy-6-methyl-4-oxo-2,3,3a,4-tetrahydro-1H-pyrrolo[2,3-b]quinolin-1-yl)benzoic acid;

3a-hydroxy-1-(3-hydroxyphenyl)-6-methyl-3,3a-dihydro-1H-pyrrolo[2,3-b]quinolin-4(2H)-one;

3a-hydroxy-1-(4-hydroxyphenyl)-6-methyl-3,3a-dihydro-1H-pyrrolo[2,3-b]quinolin-4(2H)-one;

1-(3-aminophenyl)-3a-hydroxy-6-methyl-3,3a-dihydro-1H-pyrrolo[2,3-b]quinolin-4(2H)-one; and (4-(3a-hydroxy-6-methyl-4-oxo-2,3,3a,4-tetrahydro-1H-pyrrolo[2,3-b]quinolin-1-yl)phenyl)phosphonic acid.

20. The method of claim 8, wherein the compound is the (S)-enantiomer.

21. The method of claim 8, wherein $Q_3$ is methyl and $Q_1$, $Q_2$, $Q_4$, $R_1$, $R_2$, $R_4$ and $R_5$ are hydrogen; and $R_3$ is a hydrophilic group selected from phosphonic acid, phosphoryl, hydroxyl, amino, carboxyl and ester having a C1-C4 alkyl chain.

22. The method of claim 8, wherein the compound is selected from:

1-(4-aminophenyl)-3a-hydroxy-6-methyl-3,3a-dihydro-1H-pyrrolo[2,3-b]quinolin-4(2H)-one;

3-(3a-hydroxy-6-methyl-4-oxo-2,3,3a,4-tetrahydro-1H-pyrrolo[2,3-b]quinolin-1-yl)benzoic acid;

4-(3a-hydroxy-6-methyl-4-oxo-2,3,3a,4-tetrahydro-1H-pyrrolo[2,3-b]quinolin-1-yl)benzoic acid;

3a-hydroxy-1-(3-hydroxyphenyl)-6-methyl-3,3a-dihydro-1H-pyrrolo[2,3-b]quinolin-4(2H)-one;

3a-hydroxy-1-(4-hydroxyphenyl)-6-methyl-3,3a-dihydro-1H-pyrrolo[2,3-b]quinolin-4(2H)-one;

1-(3-aminophenyl)-3a-hydroxy-6-methyl-3,3a-dihydro-1H-pyrrolo[2,3-b]quinolin-4(2H)-one; and (4-(3a-hydroxy-6-methyl-4-oxo-2,3,3a,4-tetrahydro-1H-pyrrolo[2,3-b]quinolin-1-yl)phenyl)phosphonic acid.

* * * * *